US012620211B2

(12) United States Patent
Ohara

(10) Patent No.: US 12,620,211 B2
(45) Date of Patent: May 5, 2026

(54) PROCESSING SYSTEM, IMAGE PROCESSING METHOD, LEARNING METHOD, AND PROCESSING DEVICE

(71) Applicant: OLYMPUS CORPORATION, Tokyo (JP)

(72) Inventor: Satoshi Ohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 18/952,123

(22) Filed: Nov. 19, 2024

(65) Prior Publication Data
US 2025/0078483 A1 Mar. 6, 2025

Related U.S. Application Data

(63) Continuation of application No. 17/940,224, filed on Sep. 8, 2022, now Pat. No. 12,169,963, which is a
(Continued)

(51) Int. Cl.
*A61B 90/00* (2016.01)
*A61B 1/00* (2006.01)
(Continued)

(52) U.S. Cl.
CPC ........ *G06V 10/776* (2022.01); *A61B 1/00006* (2013.01); *A61B 1/0655* (2022.02);
(Continued)

(58) Field of Classification Search
CPC .... G06V 10/776; G06V 10/25; G06V 10/774; G06V 10/87; G06V 10/141;
(Continued)

(56) References Cited

U.S. PATENT DOCUMENTS

| | | | |
|---|---|---|---|
| 11,123,047 B2 * | 9/2021 | Jaffer | A61B 8/5261 |
| 2015/0216398 A1 * | 8/2015 | Yang | G01J 3/0208 |
| | | | 600/109 |

(Continued)

FOREIGN PATENT DOCUMENTS

| | | |
|---|---|---|
| WO | 2018159461 A1 | 9/2018 |
| WO | 2018225448 A1 | 12/2018 |

(Continued)

OTHER PUBLICATIONS

International Search Report dated Apr. 14, 2020 issued in PCT/JP2020/010541.
(Continued)

*Primary Examiner* — Howard D Brown, Jr.
(74) *Attorney, Agent, or Firm* — Scully, Scott, Murphy & Presser, P.C.

(57) ABSTRACT

A processing system includes a processor with hardware. The processor is configured to perform processing of acquiring a detection target image captured by an endoscope apparatus, controlling the endoscope apparatus based on control information, detecting a region of interest included in the detection target image based on the detection target image for calculating estimated probability information representing a probability of the detected region of interest, identifying the control information for improving the estimated probability information related to the region of interest within the detection target image based on the detection target image, and controlling the endoscope apparatus based on the identified control information.

14 Claims, 15 Drawing Sheets

Related U.S. Application Data continuation of application No. PCT/JP2020/010541, filed on Mar. 11, 2020.

(51) Int. Cl.

| | |
|---|---|
| *A61B 1/06* | (2006.01) |
| *G06V 10/25* | (2022.01) |
| *G06V 10/70* | (2022.01) |
| *G06V 10/774* | (2022.01) |
| *G06V 10/776* | (2022.01) |
| *G06V 20/40* | (2022.01) |
| *H04N 23/60* | (2023.01) |
| *H04N 23/61* | (2023.01) |
| *G06V 10/141* | (2022.01) |
| *H04N 23/50* | (2023.01) |

(52) U.S. Cl.

CPC ............ *G06V 10/25* (2022.01); *G06V 10/774* (2022.01); *G06V 10/87* (2022.01); *H04N 23/61* (2023.01); *H04N 23/64* (2023.01); *G06V 10/141* (2022.01); *H04N 23/555* (2023.01)

(58) Field of Classification Search

CPC ................ G06V 2201/03; G06V 10/82; A61B 1/00006; A61B 1/0655; A61B 1/0638; A61B 1/0684; A61B 1/000096; A61B 1/000094; A61B 1/045; H04N 23/61; H04N 23/64; H04N 23/555; H04N 23/617

See application file for complete search history.

(56) References Cited

U.S. PATENT DOCUMENTS

| | | | | |
|---|---|---|---|---|
| 2019/0374088 | A1 * | 12/2019 | Watanabe | A61B 1/0638 |
| 2019/0380617 | A1 * | 12/2019 | Oosake | A61B 5/1032 |
| 2020/0193236 | A1 * | 6/2020 | Oosake | G06V 10/454 |
| 2020/0279368 | A1 | 9/2020 | Tada et al. | |
| 2020/0337537 | A1 * | 10/2020 | Hirasawa | A61B 1/000096 |
| 2021/0044750 | A1 * | 2/2021 | Kamon | A61B 1/0646 |
| 2021/0076917 | A1 * | 3/2021 | Kamon | A61B 1/0661 |
| 2021/0313052 | A1 * | 10/2021 | Makrinich | G11B 27/28 |
| 2023/0005247 | A1 * | 1/2023 | Ohara | G06V 10/776 |
| 2024/0303984 | A1 * | 9/2024 | Sanchez-Matilla | G06V 10/25 |
| 2024/0423463 | A1 * | 12/2024 | Ito | A61B 1/0655 |
| 2025/0078483 | A1 * | 3/2025 | Ohara | A61B 1/000094 |
| 2025/0157628 | A1 * | 5/2025 | Barve | G06V 10/25 |

FOREIGN PATENT DOCUMENTS

| | | |
|---|---|---|
| WO | 2019054045 A1 | 3/2019 |
| WO | 2019088121 A1 | 5/2019 |

OTHER PUBLICATIONS

US Office Action dated Mar. 13, 2024 received in U.S. Appl. No. 17/940,224.

* cited by examiner

| CONTROL INFORMATION | | |
|---|---|---|
| LIGHT SOURCE | | WAVELENGTH |
| | | LIGHT QUANTITY RATIO (COLOR BALANCE) |
| | | LIGHT QUANTITY |
| | | Duty |
| | | LIGHT DISTRIBUTION |
| IMAGING | | FRAME RATE |
| IMAGE PROCESSING | | COLOR MATRIX |
| | | STRUCTURE HIGHLIGHTING |
| | | NR |
| | | AGC |

FIG. 9A

| SECOND INPUT IMAGE | CONTROL INFORMATION | PRIORITY PARAMETER TYPE |
|---|---|---|
|  | $p_1, p_2 \cdots p_N$ | $P_k$ |

FIG. 9B

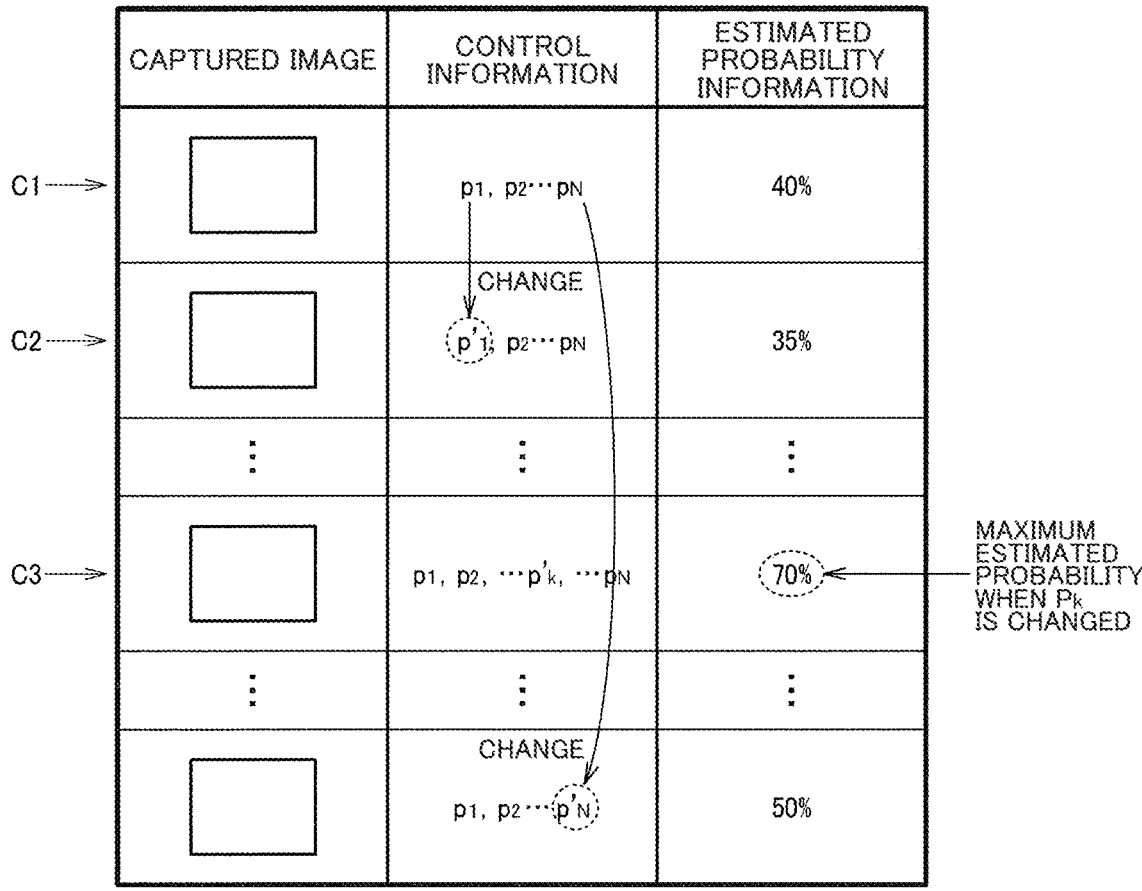

| CAPTURED IMAGE | CONTROL INFORMATION | ESTIMATED PROBABILITY INFORMATION |
|---|---|---|
| C1 → | $p_1, p_2 \cdots p_N$ | 40% |
| C2 → | CHANGE $p'_1, p_2 \cdots p_N$ | 35% |
| ⋮ | ⋮ | ⋮ |
| C3 → | $p_1, p_2, \cdots p'_k, \cdots p_N$ | 70% ← MAXIMUM ESTIMATED PROBABILITY WHEN $P_k$ IS CHANGED |
| ⋮ | ⋮ | ⋮ |
|  | CHANGE $p_1, p_2 \cdots p'_N$ | 50% |

FIG. 9C

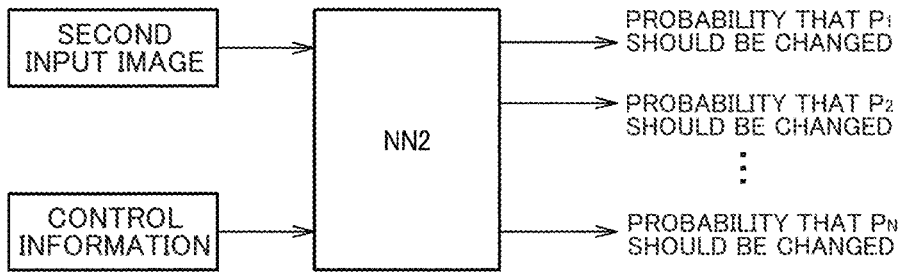

SECOND INPUT IMAGE → NN2 → PROBABILITY THAT $P_1$ SHOULD BE CHANGED

CONTROL INFORMATION → NN2 → PROBABILITY THAT $P_2$ SHOULD BE CHANGED

⋮

PROBABILITY THAT $P_N$ SHOULD BE CHANGED

FIG. 14A
| SECOND INPUT IMAGE | CONTROL INFORMATION | PRIORITY PARAMETER TYPE | RECOMMENDED VALUE |
|---|---|---|---|
|  | $p_1, p_2 \cdots p_N$ | $P_k$ | $p_k{}'$ |
FIG. 14B
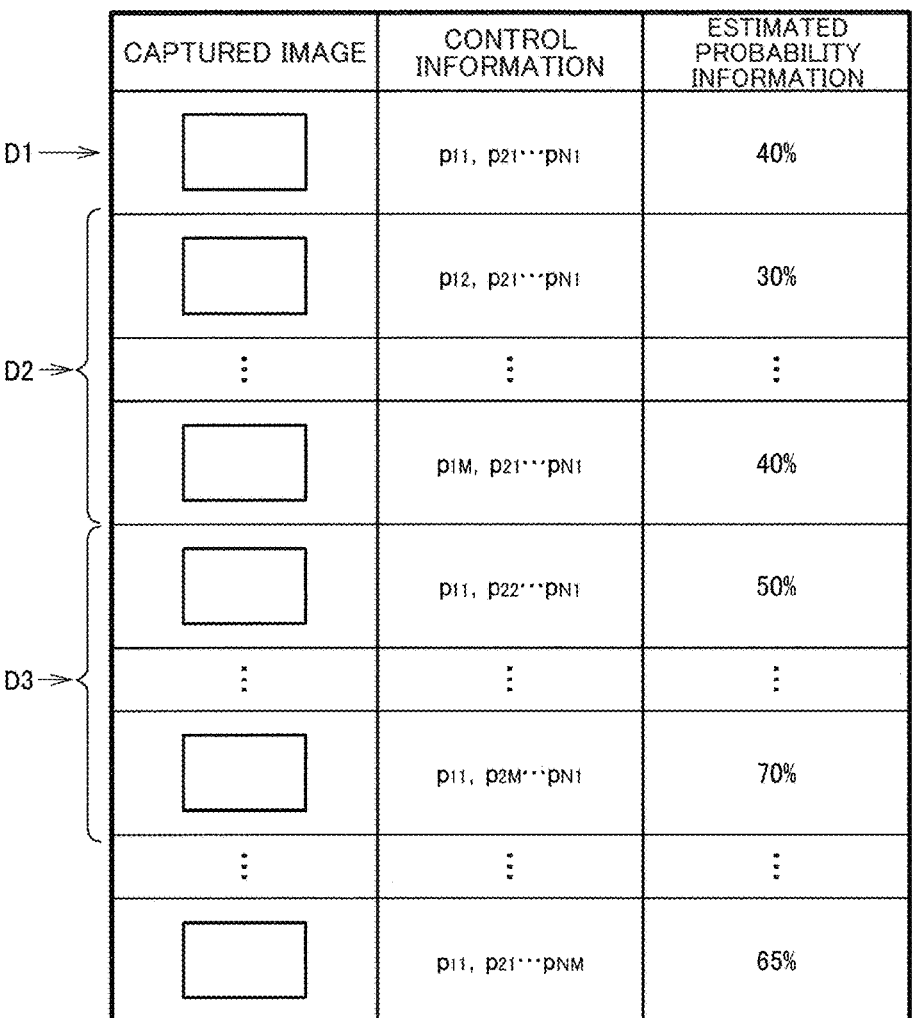
| | CAPTURED IMAGE | CONTROL INFORMATION | ESTIMATED PROBABILITY INFORMATION |
|---|---|---|---|
| D1 → |  | $p_{11}, p_{21} \cdots p_{N1}$ | 40% |
| D2 → |  | $p_{12}, p_{21} \cdots p_{N1}$ | 30% |
| | ⋮ | ⋮ | ⋮ |
| |  | $p_{1M}, p_{21} \cdots p_{N1}$ | 40% |
| D3 → |  | $p_{11}, p_{22} \cdots p_{N1}$ | 50% |
| | ⋮ | ⋮ | ⋮ |
| |  | $p_{11}, p_{2M} \cdots p_{N1}$ | 70% |
| | ⋮ | ⋮ | ⋮ |
| |  | $p_{11}, p_{21} \cdots p_{NM}$ | 65% |
FIG. 14C
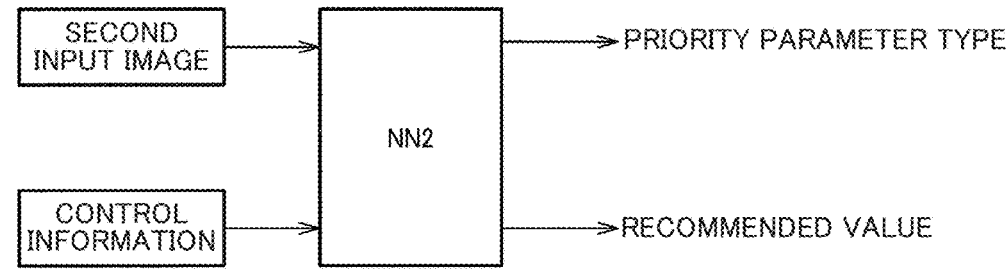

| SECOND INPUT IMAGE | CONTROL INFORMATION | RECOMMENDED CONTROL INFORMATION |
|---|---|---|
|  | $p_1, p_2 \cdots p_N$ | $p_1', p_2' \cdots p_N'$ |

PROCESSING SYSTEM, IMAGE PROCESSING METHOD, LEARNING METHOD, AND PROCESSING DEVICE

CROSS REFERENCE TO RELATED APPLICATION

This application is a continuation application of U.S. patent application Ser. No. 17/940,224 filed Sep. 8, 2022, which is a continuation of International Patent Application No. PCT/JP2020/010541, having an international filing date of Mar. 11, 2020, which designated the United States, the entirety of each of which are incorporated herein by reference.

BACKGROUND

It has been known that the image diagnosis support device for supporting a physician's diagnosis by means of an endoscopic image is configured to utilize machine learning to perform processing of detecting the lesion and acquiring estimated probability indicating the degree of detection accuracy. The neural network has been known as the trained model generated by machine learning. International Publication No. WO 2019/088121 discloses the system which provides support information by estimating information concerning name/position of a lesion, and probability thereof based on a CNN (Convolutional Neural Network) so that the estimated information is superposed on an endoscopic image.

SUMMARY

In accordance with one of some aspect, there is provided a processing system comprising a processor including hardware, wherein the processor is configured to perform processing of: acquiring a detection target image captured by an endoscope apparatus; controlling the endoscope apparatus based on control information; detecting a region of interest included in the detection target image based on the detection target image for calculating estimated probability information representing a probability of the detected region of interest; identifying the control information for improving the estimated probability information related to the region of interest within the detection target image based on the detection target image; and controlling the endoscope apparatus based on the identified control information.

In accordance with one of some aspect, there is provided an image processing method comprising: acquiring a detection target image captured by an endoscope apparatus; detecting a region of interest included in the detection target image to calculate estimated probability information representing a probability of the detected region of interest based on the detection target image; and when using information for controlling the endoscope apparatus as control information, identifying the control information for improving the estimated probability information related to the region of interest within the detection target image based on the detection target image.

In accordance with one of some aspect, there is provided a learning method for generating a trained model, comprising: acquiring an image captured by an endoscope apparatus as an input image; when using information for controlling the endoscope apparatus as control information, acquiring first control information as the control information for acquiring the input image; acquiring second control information as the control information for improving estimated probability information which represents a probability of the region of interest detected from the input image; and generating trained model by performing machine learning of a relationship among the input image, the first control information, and the second control information.

In accordance with one of some aspect, there is provided a processing device comprising a processor including hardware, wherein the processor is configured to perform processing of: acquiring a detection target image captured by an endoscope apparatus; detecting a region of interest included in the detection target image to calculate estimated probability information which represents a probability of the detected region of interest based on the detection target image; identifying the control information for improving the estimated probability information related to the region of interest within the detection target image based on the detection target image; and outputting the identified control information.

BRIEF DESCRIPTION OF THE DRAWINGS

FIG. 9A illustrates a training data example for NN2;

FIG. 9B illustrates a data example for acquiring training data;

FIG. 9C illustrates an example of input/output operation of NN2;

FIG. 14A illustrates a training data example for NN2;

FIG. 14B illustrates an example of data for acquiring training data;

FIG. 14C illustrates an example of input/output operation of NN2;

DESCRIPTION OF EXEMPLARY EMBODIMENTS

Figure 1:
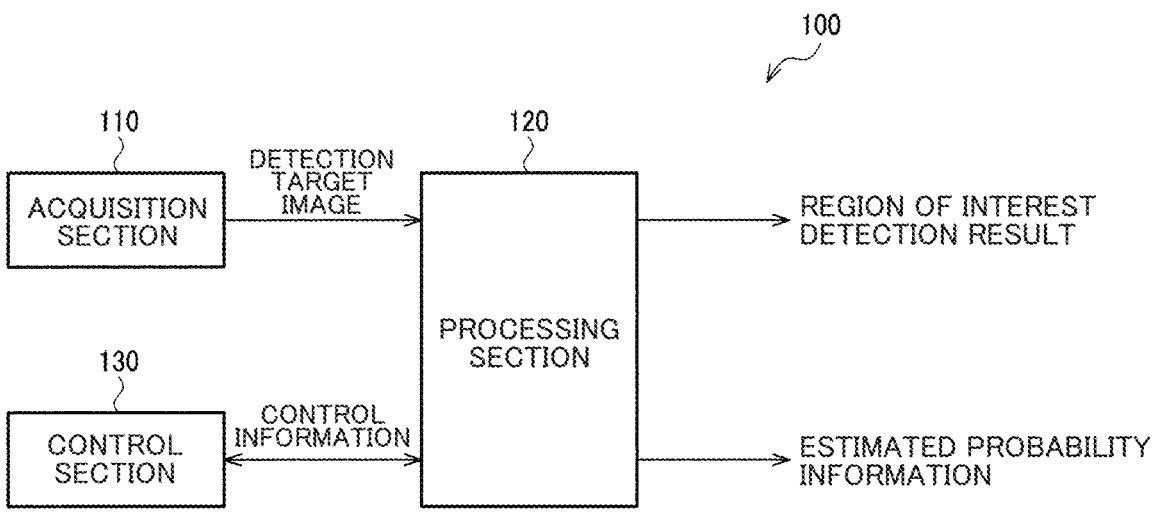
FIG. 1 illustrates a configuration example of a processing system.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

Exemplary embodiments are described below. Note that the following exemplary embodiments do not in any way limit the scope of the content defined by the claims laid out herein. Note also that all of the elements described in the present embodiment should not necessarily be taken as essential elements.

1. System Configuration

The generally employed system as disclosed in International Publication No. WO 2019/088121 is configured to display an estimated probability that represents the degree of estimation accuracy using the trained model. In the case of low estimated probability, the estimated result is not displayed to suppress provision of the low-accurate information to the user. The foregoing technique does not consider measures to be taken for improving the estimated probability derived from the trained model.

For example, in order to cope with the low estimated probability owing to a dark captured image of lesion, such measures as raising the dimming target value in the dimming processing may be taken to capture the bright image of lesion, resulting in improved estimated probability. However, the control performed by the generally employed technique merely allows the estimated probability to be displayed, or not to be displayed because of low estimated probability. In order to control the light source and the like, the user has to determine the need of changing the light intensity of the light source based on the displayed image and the like. Furthermore, the user has to execute the specific operation for changing the light intensity based on the determination. In other words, the generally employed system provides only the result of processing to the input image, leaving the task to the user for capturing the image suitable for detection of the lesion or the like.

FIG. 1 illustrates a configuration of a processing system 100 according to the present embodiment. The processing system 100 includes an acquisition section 110, a processing section 120, and a control section 130.

The acquisition section 110 is an interface for acquiring images, for example, an interface circuit for acquiring a signal from an image sensor 312 via a signal line included in a universal cable 310c. The acquisition section 110 may be provided with a pre-processing section 331 to be described later referring to FIG. 3. The processing system 100 may be included in an information processing device for acquiring the image signal output from a scope section 310 via the network. In this case, the acquisition section 110 serves as a communication interface such as a communication chip.

The processing section 120 and the control section 130 are constituted by hardware as described below. The hardware includes at least one of a circuit for processing digital signals and a circuit for processing analog signals. The hardware may be configured to include one or more circuit devices, or one or more circuit elements, which are mounted on the circuit substrate. For example, an IC (Integrated Circuit), an FPGA (Field-programmable Gate Array), and the like may be employed for one or more circuit devices. For example, a resistance, a capacitor, and the like may be employed for one or more circuit elements.

The following processor may be employed for implementing the processing section 120 and the control section 130. The processing system 100 includes a memory for storing information, and a processor operated based on the information stored in the memory. The information may be programs and various kinds of data, for example. The processor includes the hardware. Various types of processors may be used, for example, a CPU (Central Processing Unit), a GPU (Graphics Processing Unit), a DSP (Digital Signal Processor), and the like. The memory may be a semiconductor memory such as a SRAM (Static Random Access Memory) and a DRAM (Dynamic Random Access Memory), a register, a magnetic storage device such as an HDD (Hard Disk Drive), and an optical storage device such as an optical disk device. For example, the memory stores computer readable instructions. The processor executes the instruction to implement functions of the processing section 120 and the control section 130 as processing. The instruction herein may be an instruction set constituting the program, or the one for commanding a hardware circuit of the processor to carry out the operation. The processing section 120 and the control section 130 may be implemented by a single processor or different processors. The function of the processing section 120 may be implemented through distributed processing performed by multiple processors. This applies to the control section 130.

The acquisition section 110 acquires a detection target image captured by an endoscope apparatus. The endoscope apparatus herein partially or fully constitutes an endoscope system 300 to be described later referring to FIG. 2, for example. The endoscope apparatus constitutes a part of the endoscope system 300 including a scope section 310, a light source device 350, and a processing device 330.

The control section 130 controls the endoscope apparatus based on the control information. As described later referring to FIG. 4, operations for controlling the endoscope apparatus performed by the control section 130 include controlling operations of a light source 352 of the light source device 350, imaging conditions using the image sensor 312, image processing performed by the processing device 330, and the like.

Based on the trained model and the detection target image, the processing section 120 detects a region of interest included in the detection target image, and calculates the estimated probability information indicating accuracy of the detected region of interest. Based on the detection target image, the processing section 120 of the present embodiment identifies the control information for improving the estimated probability information related to the region of interest in the detection target image. Based on the identified control information, the control section 130 controls the endoscope apparatus.

The trained model herein is acquired through machine learning for calculating the estimated probability information of the region of interest in the input image. More specifically, the trained model is acquired through the machine learning based on a data set having the input image correlated with information for identifying the region of interest included in the input image. Upon input of an image, the trained model outputs a result of detecting the region of interest of the target image, and the estimated probability information indicating a probability of the detection result. Although description will be given below of an example in which the estimated probability information is the estimated probability itself, the estimated probability information may be the information as an index indicating the estimation probability, and may be different from the estimated probability.

The region of interest in the present embodiment refers to the region to be observed by the user with relatively higher priority than the other region. If the user is a physician who performs diagnosis and treatment, the region of interest corresponds to the region which reflects a lesion part, for example. If the physician requires to observe bubbles or feces, the region reflecting the bubbles or feces may be the region of interest. That is, the target of user's interest varies depending on the observation purpose. In the observation, the region to be observed by the user with relatively higher priority than that of the other region becomes the region of interest.

The processing system 100 of the present embodiment performs not only processing of obtaining the estimated probability, but also processing of identifying the control information for improving the estimated probability. The control information includes information data corresponding to various parameter types as described later referring to FIG. 4. For example, in order to improve the estimated probability, the processing section 120 determines which parameter type should be changed and what value should be used for the parameter value of the parameter type.

The control section 130 performs the control using the control information identified by the processing section 120. Accordingly, the newly acquired detection target image as the control result is expected to have the estimated probability of the region of interest further improved than the one before changing the control information. In other words, the processing system 100 of the present embodiment itself is allowed to carry out the cause analysis for improving the estimated probability and modification of control conditions. This makes it possible to provide highly reliable information while suppressing increase in the load of the user.

Figure 2:
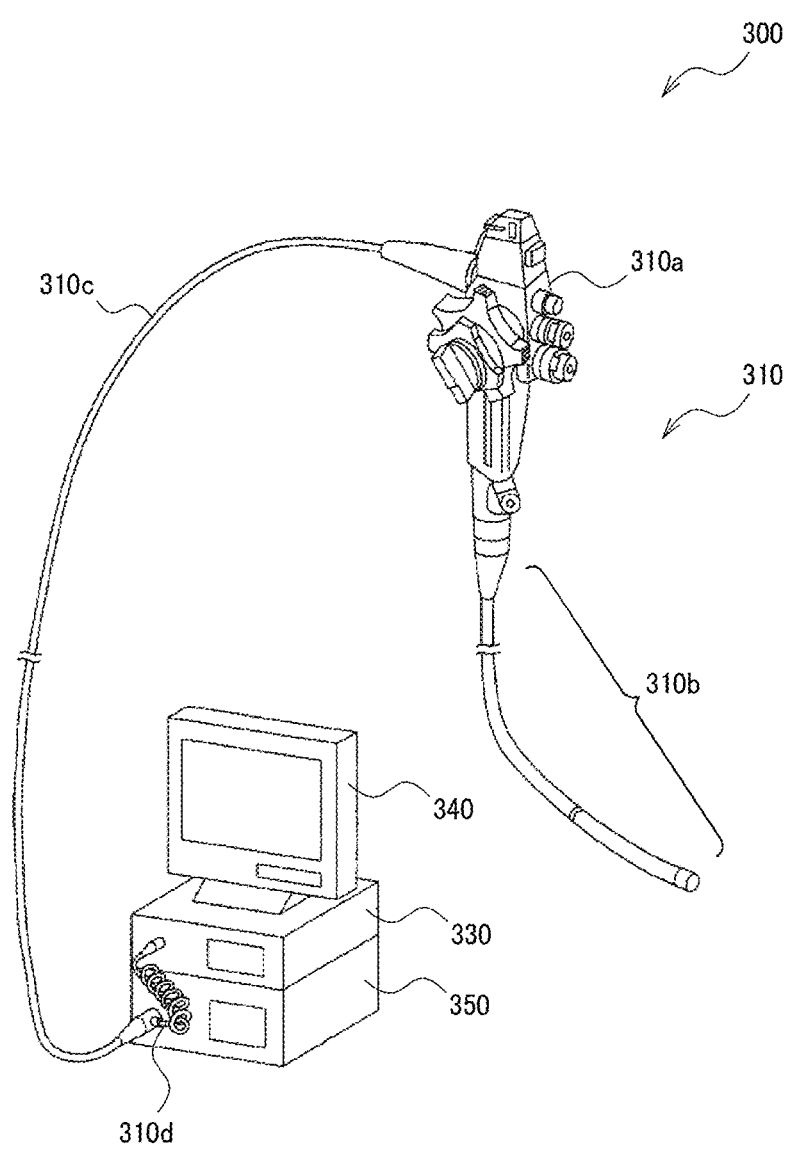
FIG. 2 illustrates an external appearance of an endoscope system.

FIG. 2 illustrates a configuration of the endoscope system 300 including the processing system 100. The endoscope system 300 includes the scope section 310, the processing device 330, a display section 340, and the light source device 350. For example, the processing system 100 is included in the processing device 330. The physician performs an endoscopy on a patient using the endoscope system 300. The configuration of the endoscope system 300 is not limited to the one as illustrated in FIG. 2, but may be variously modified by omitting a part of the components, or adding other components. The following explanation will be made with respect to the use of a flexible mirror for diagnosis of digestive organs as an exemplified case. The scope section 310 of the present embodiment may be a hard mirror used for a laparoscopic surgery operation (laparoscopic procedures). The endoscope system 300 is not limited to the medical endoscope for in-vivo observation, but may be formed into to an industrial endoscope.

Referring to FIG. 2, the processing device 330 is a single unit connected to the scope section 310 via a connector 310d as an exemplified case, which is not limited thereto. For example, the processing device 330 may be partially or fully configured by a PC (Personal Computer) and other information processing device such as a server system, which are connectable via the network. For example, cloud computing may be used to implement the processing device 330. The network herein may be a private network such as Intranet, or public telecommunication network such as Internet. The network may be wired or wireless. That is, configuration of the processing system 100 is not limited to the one included in the device to be connected to the scope section 310 via the connector 310d. Functions of the processing system 100 may be partially or fully implemented by other devices such as a PC, or by cloud computing.

The scope section 310 includes an operation section 310a, a flexible insertion section 310b, and a universal cable 310c including a signal line. The scope section 310 is a tubular insertion device for inserting the tubular insertion section 310b into a body cavity. The connector 310d is attached to an end of the universal cable 310c. The scope section 310 is detachably attached to the light source device 350 and the processing device 330 using the connector 310d. As described later referring to FIG. 3, a light guide 315 is inserted into the universal cable 310c. The scope section 310 emits illumination light of the light source device 350 from a leading end of the insertion section 310b through the light guide 315.

For example, the insertion section 310b includes the leading end portion, a curve portion which can be curved, and a flexible tube portion, which are positioned from the leading end to a base end of the insertion section 310b. The insertion section 310b is inserted into an object. The leading end portion of the insertion section 310b constitutes a hard tip end member formed at the leading end of the scope section 310. An objective optical system 311 or an image sensor 312 which will be described later are attached to the leading end portion, for example.

The curve portion can be curved in a desired direction by operating a curving operation member provided in the operation section 310a. The curving operation member includes left-right and up-down curving operation knobs, for example. The operation section 310a may be provided with various operation buttons, for example, a release button, a gas/water supply button, or the like in addition to the curving operation member.

The processing device 330 is a video processor configured to perform predetermined image processing to a received captured signal, and generate a captured image. The video signal of the generated captured image is output from the processing device 330 to the display section 340 on which a live captured image is displayed. A structure of the processing device 330 will be described later. The display section 340 may be a liquid crystal display, an EL (Electro-Luminescence) display, or the like.

The light source device 350 is capable of emitting normal light for a normal light observation mode. If the endoscope system 300 has a special light observation mode in addition to the normal light observation mode, the light source device 350 emits the normal light for the normal light observation mode and the special light for the special light observation mode selectively.

Figure 3:
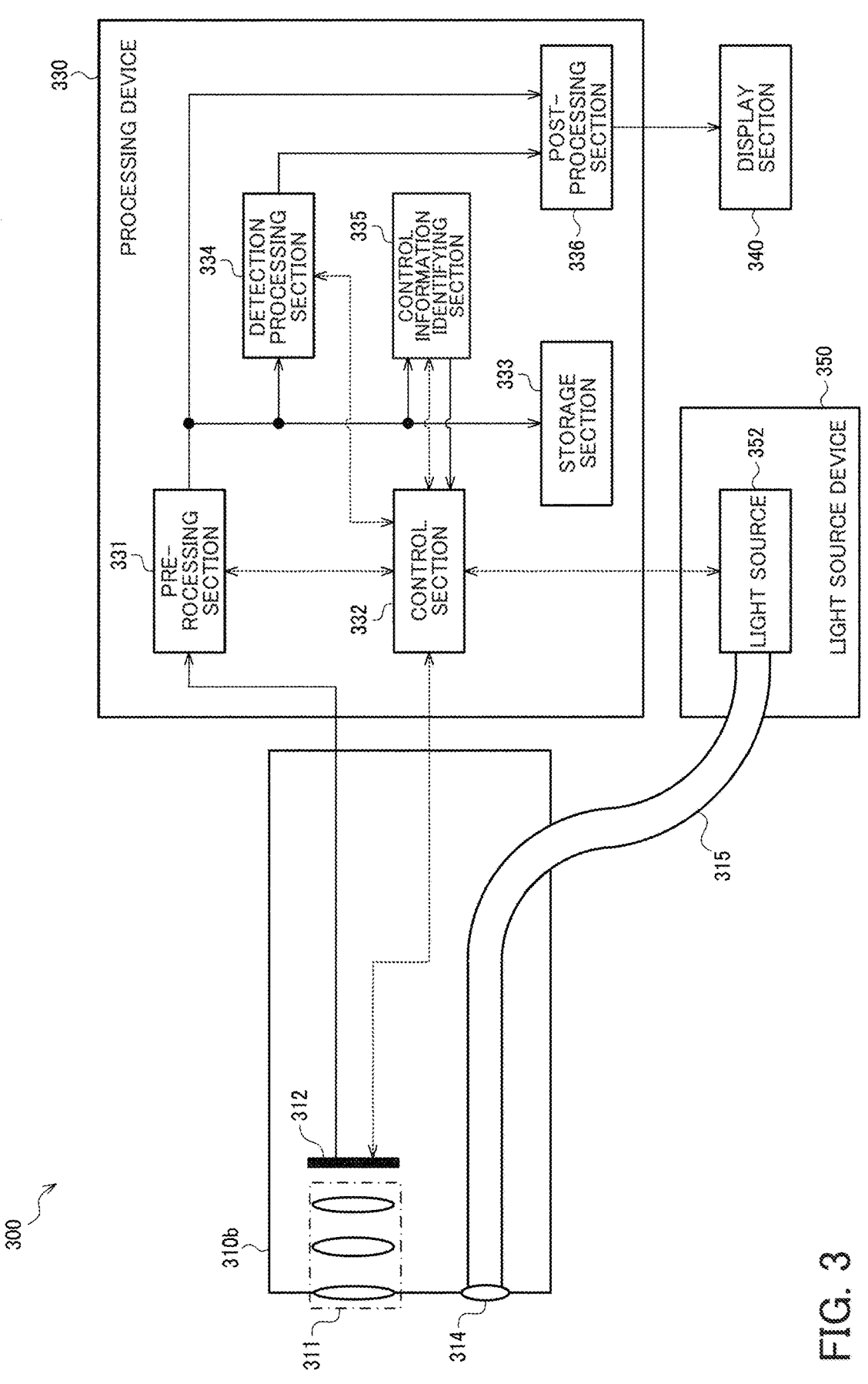
FIG. 3 illustrates a configuration example of an endoscope system.

FIG. 3 illustrates configuration of components constituting the endoscope system 300. FIG. 3 partially omits the structure of the scope section 310 for simplification.

The light source device 350 includes the light source 352 which emits illustration light. The light source 352 may be a xenon light source, an LED (light emitting diode), or a laser light source. The light source 352 may be other light source without being limited to the light emission type.

The insertion section 310b includes the objective optical system 311, the image sensor 312, an illumination lens 314, and a light guide 315. The light guide 315 guides the illumination light from the light source 352 to the leading end of the insertion section 310b. The illumination lens 314 irradiates the object with the illumination light guided by the light guide 315. The objective optical system 311 forms the reflected light reflected from the object into an object image. The objective optical system 311 may be configured to have a focus lens which makes the object image forming position variable in accordance with a position of the focus lens. For example, the insertion section 310b may be configured to have a not shown actuator which drives the focus lens based on the control from a control section 332. In this case, the control section 332 performs an AF (AutoFocus) control operation.

The image sensor 312 receives the light from the object via the objective optical system 311. The image sensor 312 may be a monochrome sensor, or an element provided with a color filter. The color filter may be a known Bayer filter, a complementary color filter, or any other filter. The complementary color filter includes a cyan color filter, a magenta color filter, and a yellow color filter.

The processing device 330 performs operations for image processing and overall system controlling. The processing device 330 includes the pre-processing section 331, the control section 332, a storage section 333, a detection processing section 334, a control information identifying section 335, and a post-processing section 336. For example, the pre-processing section 331 corresponds to the acquisition section 110 of the processing system 100. The detection processing section 334 and the control information identifying section 335 correspond to the processing section 120 of the processing system 100. The control section 332 corresponds to the control section 130 of the processing system 100.

The pre-processing section 331 performs A/D conversion for converting an analog signal sequentially output from the image sensor 312 into a digital image, and various kinds of correction processing to the A/D converted image data. The image sensor 312 may be provided with an A/D conversion circuit by omitting the A/D conversion performed by the pre-processing section 331. The correction processing herein includes processing such as color matrix correction, structure highlighting, noise reduction, AGC (automatic gain control), and the like as described later referring to FIG. 4, for example. The pre-processing section 331 may be configured to perform other correction processing such as white balance processing. The pre-processing section 331 outputs the processed image to the detection processing section 334 and the control information identifying section 335 as the detection target image. The pre-processing section 331 outputs the processed image to the post-processing section 336 as a display image.

The detection processing section 334 performs detection processing for detecting the region of interest from the detection target image. The detection processing section 334 outputs an estimated probability representing probability of the detected region of interest. For example, the detection processing section 334 is operated in accordance with the trained model information stored in the storage section 333 so that the detection processing is performed.

In the present embodiment, a single kind of region of interest may be detected. For example, in the case of a polyp as the region of interest, the detection processing may be performed for identifying the position and size of the polyp in the detection target image. In the present embodiment, multiple types of regions of interest may be set. For example, in the known classification process, the polyp is classified into TYPE1, TYPE2A, TYPE2B, and TYPE3 depending on the condition. The detection processing of the present embodiment may include processing of classifying the polyp into one of the types as described above besides the processing of merely detecting the position and size of the polyp. The estimated probability in this case is the information indicating probability of the position/size of the region of interest, and the classification result.

The control information identifying section 335 performs processing of identifying the control information for improving the estimated probability based on the detection target image. The processing performed by the detection processing section 334 and the control information identifying section 335 will be described in detail later.

The post-processing section 336 performs post-processing based on the detection result of the region of interest, which has been derived from the detection processing section 334, and outputs the post-processed image to the display section 340. The post-processing herein is performed for adding the detection result based on the detection target image to the display image, for example. As an explanation will be made later referring to FIG. 12, for example, the display image and the detection target image are alternately acquired. As an explanation will be made later referring to FIG. 13A and FIG. 13B, the detection result of the region of interest refers to, in a narrow sense, the information for supporting the user with diagnosis or the like. Accordingly, the detection target image of the present embodiment may be rephrased as a support image for supporting the user. The detection result of the region of interest may be rephrased as support information.

The control section 332 is interconnected to the image sensor 312, the pre-processing section 331, the detection processing section 334, the control information identifying section 335, and the light source 352 so that the respective sections and components are controlled. Specifically, the control section 332 controls the respective components of the endoscope system 300 based on the control information.

Figures 4, 5:
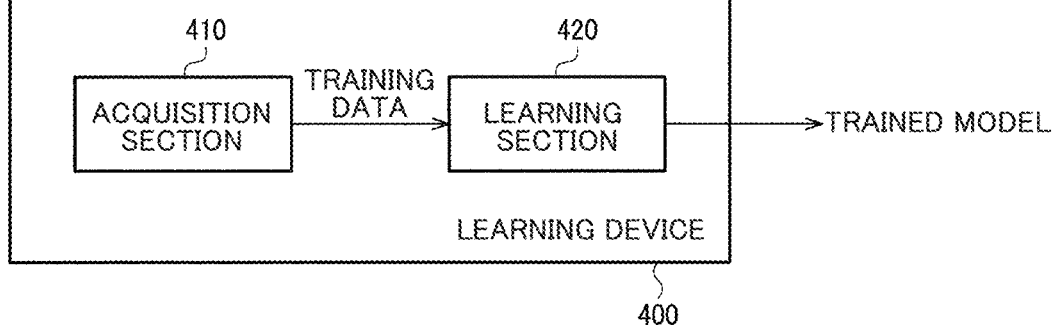
FIG. 4 illustrates a control information example.
FIG. 5 illustrates a configuration example of a learning device.

FIG. 4 illustrates an example of the control information. The control information includes light source control information for controlling the light source 352, imaging control information for controlling an imaging condition for the image sensor 312, and image processing control information for controlling the image processing performed by the processing device 330.

The light source control information includes, for example, wavelength, light quantity ratio, light quantity, duty, and light distribution, as parameter types. The imaging control information includes an imaging frame rate. The image processing control information includes a color matrix, structure highlighting, noise reduction and AGC. The control information is, for example, a set of the parameter type and specific parameter value related to the parameter type. An explanation will be made with respect to specific examples of the respective parameter types and parameter values.

The wavelength represents a wavelength band of the illumination light. For example, the light source device 350 is capable of emitting the normal light and the special light, and includes multiple light sources such as a red LED, a green LED, a blue LED, a green narrowband light LED, a blue narrowband light LED, and the like. The light source device 350 emits the normal light which contains R light, G light, and B light by lighting the red LED, the green LED, and the blue LED, respectively. For example, the B light has its wavelength band ranging from 430 to 500 nm, the G light has its wavelength band ranging from 500 to 600 nm, and the R light has its wavelength band ranging from 600 to 700 nm. The light source device 350 emits the special light which contains the G2 light and the B2 light by lighting the green narrowband light LED and the blue narrowband light LED. For example, the B2 light has its wavelength band ranging from 390 to 445 nm, and the G2 light has its wavelength band ranging from 530 to 550 nm. The special light herein refers to the illumination light for NBI (Narrow Band Imaging). The light with other wavelength band using infrared light or the like has been known as the special light. The light as described above is broadly applicable to the present embodiment.

The parameter value indicating the wavelength is expressed as binary information for identifying whether the light is the normal light or NBI, for example. Alternatively, the parameter value may be set as the information for determining lighting on/off of each of the multiple LEDs. In this case, the parameter value related to the wavelength is expressed as data with bit number corresponding to the number of LEDs. The control section 332 controls lighting on/off of multiple light sources based on the parameter value related to the wavelength. Alternatively, the light source device 350 may be configured to include a white light source and a filter, and to switch the light between the normal light and the special light based on insertion/retraction or rotation of the filter. In this case, the control section 332 controls the filter based on the parameter value of the wavelength.

The light quantity refers to intensity of light emitted from the light source device 350. For example, the endoscope system 300 of the present embodiment may be configured to perform known automatic dimming processing. The automatic dimming processing is performed by, for example, determining brightness in reference to the captured image, and automatically adjust the light quantity of the illumination light based on the determination result. In the dimming processing, a dimming target value is set as a target value of brightness. The parameter value indicating the light quantity is, for example, a target light quantity value. Adjustment of the target light quantity value allows brightness of the region of interest on the image to be optimized.

The light quantity ratio refers to a ratio of intensity among multiple lights emittable by the light source device 350. For example, the light quantity ratio of the normal light corresponds to the intensity ratio among R light, G light, and B light. The parameter value related to the light quantity ratio is, for example, a numerical value obtained by normalizing each emission intensity of multiple LEDs. Based on the foregoing parameter values of light quantity and the foregoing parameter values of light quantity ratio, the control section 332 determines each emission intensity of the respective light sources, for example, the current value to be supplied to each of the light sources. The light quantity may be adjusted in accordance with the duty to be described later. The light quantity ratio in this case corresponds to, for example, the duty ratio among the respective RGB light sources. Control of the light quantity ratio allows cancellation of variation in color owing to difference among individual patients, for example.

The duty refers to a relationship between light-on time and light-off time of the light source 352, and in a narrow sense, the ratio of the light-on time to the period corresponding to the single imaging frame. The parameter value related to the duty may be, for example, the numerical value indicating the ratio as described above, or the numerical value indicating the light-on time. For example, in the case where the light source 352 performs pulse emission with repetition of light-on and light-off, duty control is performed by changing the light-on time per frame. Alternatively, the duty control may be performed by switching the continuous emission state of the light source 352 to the pulse emission state. If the light-on time is reduced without changing the light quantity per unit time, the image is darkened because of reduced total light quantity per frame. For the purpose of reducing the duty, the control section 332 may be configured to perform the control operation for raising the dimming target value described above to maintain the total light quantity per frame. Reduction in the duty may suppress blurring of the image. Increase in the duty may suppress deterioration in the LED as the total light quantity is maintained even in the case of suppressing the light quantity per unit time.

The light distribution refers to the direction-dependent light intensity. For example, in the case where multiple irradiation ports for irradiating different areas are attached to the leading end of the insertion section 310b, quantities of light emitted from the respective irradiation ports are regulated to change the light distribution. The parameter value related to the light distribution refers to, for example, the information to identify each quantity of light emitted from the irradiation ports. The use of an optical system such as a lens and a filter may control the light quantity of the illumination light in the respective directions. Specific structures for changing the light distribution may be variously modified.

For example, assuming that the insertion section 310b is moving in a lumen-like object, the object around the center of the image is farther from the leading end of the insertion section 310b than the object in the periphery of the image. As a result, the area around the periphery of the image becomes brighter than the area around the center of the image. If the leading end of the insertion section 310b substantially faces the wall surface of the object, the distance from the leading end to the object around the center of the image hardly differs from the distance from the leading end to the object in the periphery of the image. Accordingly, the area around the center of the image becomes brighter than the area in the periphery of the image. As described above, the direction in which the image is likely to become brighter or darker is variable depending on the circumstance. Control of the light distribution allows optimization of brightness of the desired region of the image.

The frame rate refers to the number of images captured per unit time. The parameter value related to the frame rate is the numerical value indicating the number of frames per second, for example. Raising the frame rate may increase the number of captured images acquired per unit time so that blurring of the image is suppressed. Reducing the frame rate may prolong the irradiation time taken by the light source 352. This allows the bright image to be easily acquired.

The color matrix refers to a matrix for obtaining each pixel value after correction based on the original RGB pixel values, for example. A parameter value related to the color matrix is a set of numerical values indicating the respective elements of the matrix. The parameter value is not limited to the matrix by itself. It is possible to use other information based on which the color tone is adjustable through conversion of RGB pixel values. The use of the color matrix allows suppression of variation in color in the similar manner to the case of controlling the light quantity ratio of the light source 352.

The structure highlighting processing refers to the digital highlighting filter processing, for example. A parameter value related to the structure highlighting refers to the information for identifying the filter property of the digital filter, for example, a set of numerical values indicating the space filter size, and the respective elements of the filter. Performing the structure highlighting processing allows the shape of the region of interest to be clarified. Excessively performing the structure highlighting processing may result in the risk of generating artifact.

Noise reduction processing refers to the smoothing filter processing, for example. A parameter value related to the noise reduction processing refers to information for identifying the smoothing filter. The information for identifying the smoothing filter may be, for example, the value of σ of the Gaussian filter, or a set of numerical values indicating the respective elements of the filter. The degree of noise reduction may be adjusted by changing the given number of filter applications. In this case, a parameter value related to the noise reduction refers to a numerical value indicating the number of applications of the smoothing filter. Performing the noise reduction processing reduces the noise included in the image so that visibility of the region of interest is improved. Excessively performing noise reduction processing may make the edge or the like of the region of interest dull.

A parameter value related to AGC refers to a numerical value indicating the gain. Increase in the gain allows the image to be brightened, but may increase the noise as well. Decrease in the gain allows suppression of noise increase, but resultant brightness of the image may be insufficient.

As described above, the control information includes various kinds of parameter type information data. Adjustment of the parameter values of parameter types changes properties of the acquired image. The control information of the present embodiment may fully contain information on all the parameter types as described above or partially omit the information. The control information may contain information on other parameter types related to the light source, imaging, and image processing.

The parameter values optimum for raising the estimated probability of the region of interest vary depending on conditions. The condition herein represents the patient as the imaging object, an organ, a type of region of interest, relative position/posture between the leading end of the insertion section 310*b* and the object, and the like. Accordingly, the process of identifying the optimum control information may impose heavy load to the user. Meanwhile, the method of the present embodiment allows automatic identification of the control information that the processing system 100 regards as appropriate as described above.

2. Processing Flow

The processing of the present embodiment will be described in detail. The learning processing for generating the trained model will be described first, and then, inference processing using the trained model will be described. The inference processing herein refers to the processing of detecting a region of interest, which is performed by the detection processing section 334. In the following description, an explanation will be made with respect to an example of using the trained model for processing of identifying the control information, which is performed by the control information identifying section 335.

2.1 Learning Processing

FIG. 5 illustrates a configuration example of a learning device 400. The learning device 400 includes an acquisition section 410 and a learning section 420. The acquisition section 410 acquires training data to be used for learning. A set of training data includes input data, and data correlated with a correct label corresponding to the input data. The learning section 420 performs machine learning based on a large volume of acquired training data to generate the trained model. The detailed explanations of the training data and the specific flow of the learning processing will be made later.

The learning device 400 refers to an information processing device such as a PC and a server system. The learning device 400 may be implemented through distributed processing performed by multiple devices. The learning device 400 may also be implemented by, for example, cloud computing using multiple servers. The learning device 400 may be integrated with the processing system 100, or serve as a device independent from the processing system 100.

An explanation will be made briefly with respect to the machine learning using the neural network. The method for machine learning according to the present embodiment is not limited to the one to be described below. In the present embodiment, the machine learning may be carried out using other model, for example, SVM (support vector machine), or through the process established by developing various methods such as the neural network and the SVM.

Figures 6A, 6B:
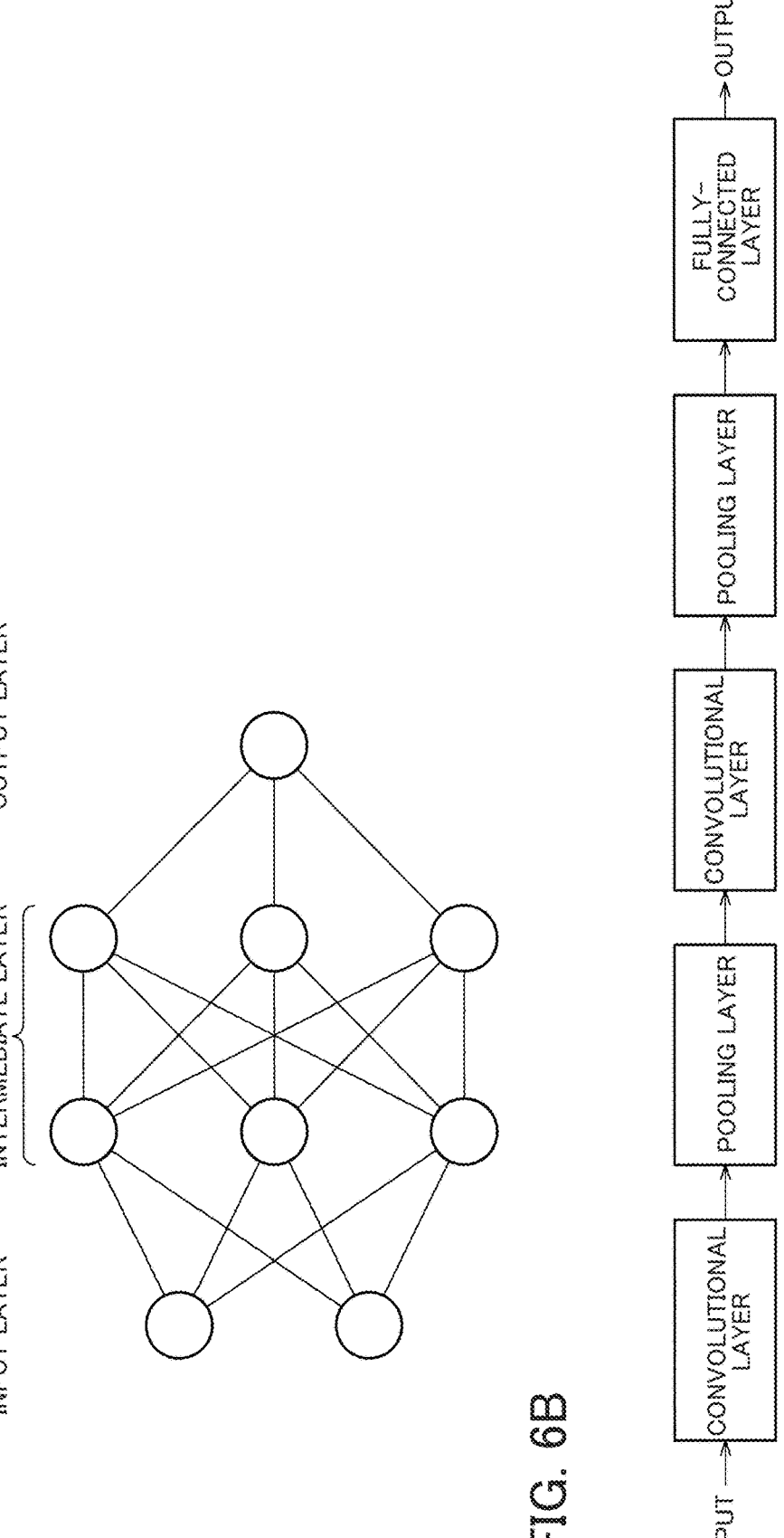
FIGS. 6A and 6B each illustrate a configuration example of a neural network.

FIG. 6A is a schematic view which illustrates the neural network including an input layer for receiving a data input, an intermediate layer for performing arithmetic operations based on an output from the input layer, and an output layer for outputting data based on an output from the intermediate layer. FIG. 6A illustrates an exemplary network with a two-layered intermediate layer. However, the intermediate layer may have one layer, or three or more layers. The number of nodes included in each layer is not limited to the example illustrated in FIG. 6A, but may be variously modified. In the present embodiment, it is preferable to employ the deep learning using multilayer neural network in consideration of accuracy. The multilayer herein refers to four or more layers in a narrow sense.

As FIG. 6A illustrates, the node included in a given layer is bound to the node included in the adjacent layer. Each weighting coefficient is set for binding the respective nodes. Each of the nodes multiplies the output from the node in the previous stage by the weighting coefficient to obtain a total value of multiplication results. The node obtains its output by adding a bias to the total value, and applying an activation function to the addition result. The processing is sequentially performed from the input layer to the output layer so that an output of the neural network is obtained. Various functions such as the sigmoid function and ReLU function each known as the activation function are broadly applicable to the present embodiment.

Learning through the neural network refers to the processing which determines the appropriate weighting coefficient. The weighting coefficient herein includes the bias. Specifically, the learning device 400 inputs the input data of the training data to the neural network, and performs the arithmetic operation in the forward direction using the corresponding weighting coefficient so that an output is obtained. The learning section 420 of the learning device 400 obtains an error function based on the output and the correct label of the training data. The weighting coefficient is updated to make the error function small. For example, it is possible to use an error back propagation method for updating the weighting coefficient from the output layer to the input layer.

The neural network may be implemented by a CNN (Convolutional Neural Network), for example. FIG. 6B is a schematic view which illustrates the CNN. The CNN includes a convolutional layer which performs a convolutional operation and a pooling layer. The convolutional layer performs the filter processing. The pooling layer performs a pooling operation for reducing longitudinal/lateral size. FIG. 6B illustrates an example of the network in which the convolutional layer and the pooling layer perform arithmetic operations multiple times, and a fully connected layer performs an arithmetic operation so that an output is obtained. The fully connected layer performs the arithmetic operation for connecting all nodes in the previous layer to the nodes of the given layer. The arithmetic operation corresponds to the one performed in each of the respective layers as illustrated in FIG. 6A. Although not illustrated in FIG. 6B, when using the CNN, the arithmetic operation with the activation function is performed similar to the case as illustrated in FIG. 6A. The CNN known to be variously configured may be broadly applied to the present embodiment. For example, the CNN of the present embodiment allows the use of the known RPN (Region Proposal Network).

The same processing procedure as the one illustrated in FIG. 6A is used for the CNN. That is, the learning device 400 inputs the input data of the training data to the CNN, and obtains an output by performing the filter processing and the pooling operation using the corresponding filter property. The error function is obtained based on the output and the correction label. The weighting coefficient including the filter property is updated to make the error function small. For example, the error back propagation method may also be used for updating the weighting coefficient for the CNN.

Figure 7A:
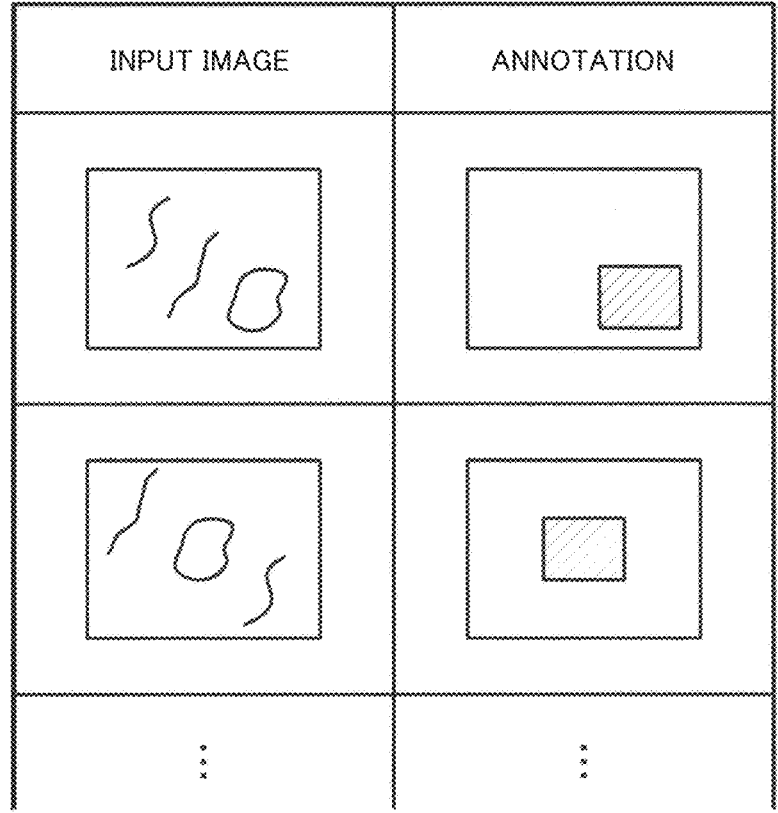
FIG. 7A illustrates a training data example for NN1.
Figure 7B:
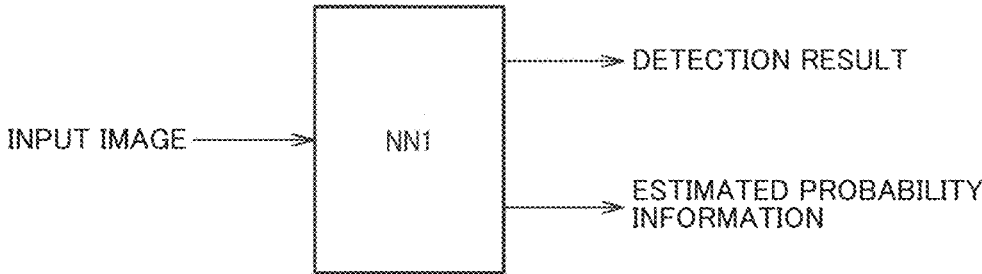
FIG. 7B illustrates an example of input/output operation of NN1.

FIG. 7A illustrates an example of the training data for generating the trained model used for detection processing performed by the detection processing section 334. In the following description, the trained model used for the detection processing will be referred to as an NN1. FIG. 7B illustrates an input/output operation of the NN1.

As FIG. 7A illustrates, the training data include input images and annotation data attached to the input images. The input image is captured by the scope section 310, specifically, an in-vivo image in a narrow sense. The annotation data refer to the information data for identifying the region of interest in the input image, which are attached by a user with specialized knowledge such as physicians. For example, as FIG. 7A illustrates, the annotation data are used for identifying position/size of a rectangular area which contains the region of interest. The rectangular area will be hereinafter referred to as a detection frame. The annotation data are configured by combining coordinates of an upper left end point and coordinates of a lower right end point of the detection frame. Alternatively, the annotation data may be configured to identify the region of interest by a unit of pixel. For example, the annotation data may be formed into a mask image having a pixel included in the region of interest set to a first pixel value, and a pixel which is not included in the region of interest set to a second pixel value.

As FIG. 7B illustrates, the NN1 receives an input of the input image, and performs an arithmetic operation in the forward direction to output the detection result and the estimated probability information. The NN1 sets a predetermined number of detection frame candidates on the input image, and performs processing of obtaining probability that the detection frame candidate is identified as the detection frame. In this case, the detection frame candidate having the probability being equal to or higher than the predetermined value is output as the detection frame. The probability correlated to the detection frame candidate employed for the detection frame is set as the estimated probability. Alternatively, the NN1 performs processing of obtaining the probability that each pixel of the input image is included in the region of interest. In this case, the set of pixels, which exhibits high probability represents the detection result of the region of interest. The estimated probability information is determined based on the probability set correlated to the pixel classified as the region of interest. Such information is expressed as statistics describing multiple numerical values representing the probability, for example. The statistic herein may be an average value, a median, or other values.

The NN1 may be configured to perform processing of classifying the region of interest. For example, the NN1 may be configured to receive an input of the input image, and perform an arithmetic operation in the forward direction to output the position/size of the region of interest, and type of the region of interest as detection results. The NN1 outputs the estimated probability information indicating the probability of the detection result. For example, the NN1 performs processing to obtain probability that the object included in the detection frame candidate is a polyp of TYPE1, TYPE2A, TYPE2B, TYPE3, and the normal mucous membrane. That is, it is possible for the detection result of the region of interest according to the present embodiment to include the type of the region of interest.

Figure 8:
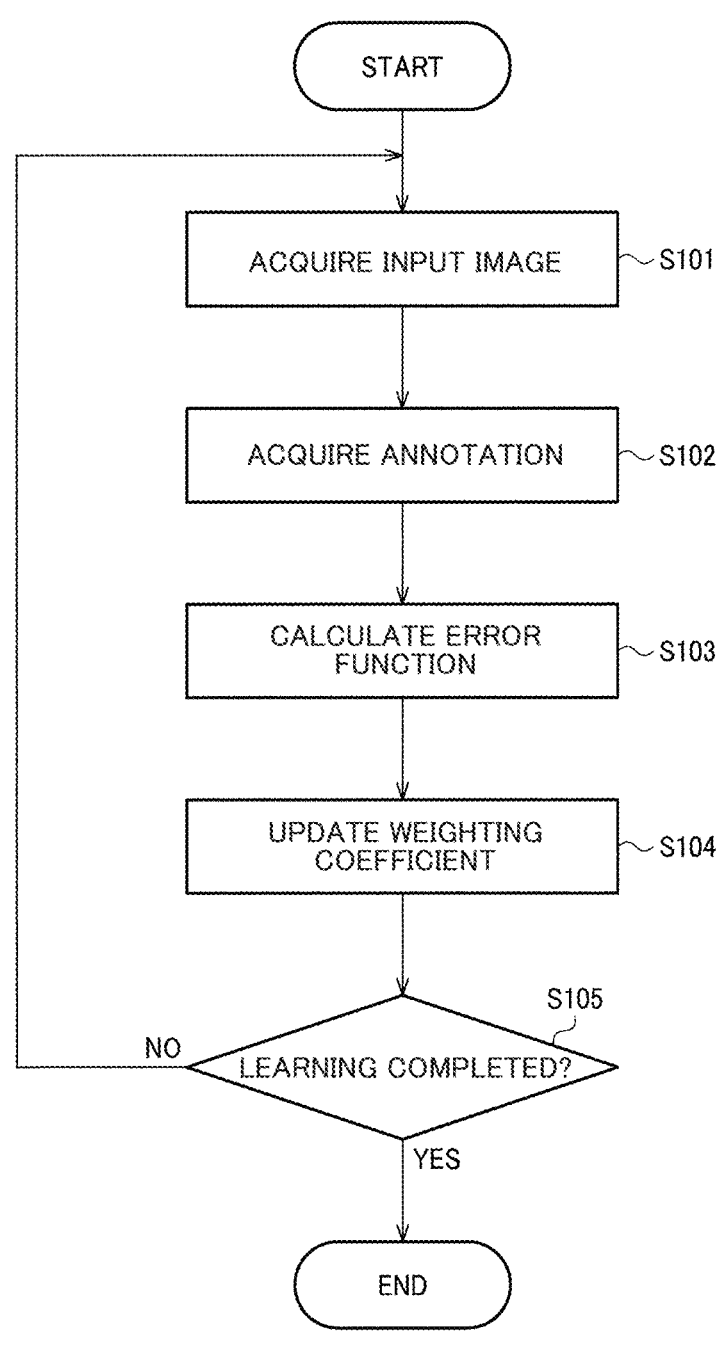
FIG. 8 illustrates a flowchart representing NN1 learning processing.

FIG. 8 is a flowchart illustrating NN1 learning processing. First, in steps S101 and S102, the acquisition section 410 acquires an input image, and annotation data attached to the input image. For example, the learning device 400 stores a large volume of training data in which the input image and the annotation data are correlated, in a not shown storage section. In steps S101 and S102, the processing is performed for retrieving one of the training data, for example.

In step S103, the learning section 420 obtains the error function. Specifically, the learning section 420 inputs the input image to the NN1, and performs an arithmetic operation in the forward direction based on the corresponding weighting coefficient. The learning section 420 obtains the error function based on comparison between the operation result and the annotation data.

In step S104, the learning section 420 updates the weighting coefficient to make the error function small. Processing in step S104 may be performed using the error back propagation method as described above. The series of processing operations in steps S101 to S104 correspond to one cycle of the learning processing based on one set of the training data.

In step S105, the learning section 420 determines whether or not the learning processing is to be finished. For example, the learning section 420 may be configured to finish the learning processing after the processing in steps from S101 to S104 the predetermined number of times. Alternatively, the learning device 400 may be configured to hold a part of a large volume of training data as verification data. The verification data are used for confirming accuracy of the learning result, and not used for updating the weighting coefficient. The learning section 420 may be configured to finish the learning processing if an accuracy rate of the estimation processing using the verification data exceeds a predetermined threshold.

If No is obtained in step S105, the process returns to step S101 where the learning processing is continuously performed based on the next training data. If Yes is obtained in step S105, the learning processing is finished. The learning device 400 transmits the generated trained model information to the processing system 100. Referring to an example of FIG. 3, the trained model information is stored in the storage section 333. It has been known that various methods such as batch learning and mini batch learning are implemented for machine learning. Those methods may be broadly applied to the present embodiment.

FIG. 9A illustrates an example of training data for generating the trained model used for the control information identifying processing performed by the control information identifying section 335. The trained model used for the control information identifying processing will be referred to as an NN2. FIG. 9B illustrates an example of data for generating the training data as illustrated in FIG. 9A. FIG. 9C illustrates an input/output operation of the NN2.

As FIG. 9A illustrates, the training data include a second input image and control information used for acquiring the second input image. The input image input to the NN1 and the second input image both have been captured using the scope section 310. Those images may be shared or different from each other. FIG. 9A illustrates an example that the control information includes N parameter types. The N parameter types will be expressed as $P_1$ to $P_N$. Each of the parameter types $P_1$ to $P_N$ corresponds to, for example, one of the wavelength, light quantity ratio, light quantity, duty, light distribution, frame rate, color matrix, structure highlighting, noise reduction, and AGC, respectively. Parameter values of the parameter types $P_1$ to $P_N$ will be expressed as $p_1$ to $p_N$, respectively. The parameter values $p_1$ to $p_N$ are related to the light source control information, the imaging control information, and the image processing control information. Based on the parameter values, emission of illumination light, imaging, and image processing are performed so that the second input image is acquired. As FIG. 9A illustrates, the training data include the information for identifying a priority parameter type.

The priority parameter type refers to the parameter type which should be preferentially changed for improving the estimated probability. The improved estimated probability represents that a second estimated probability of the second image acquired using the control information which has been changed is obtained, which becomes higher than a first estimated probability of the first image acquired using the given control information. The priority parameter type of $P_k$ represents that it has been determined that change in the parameter value of $P_k$ is likely to improve the estimated probability higher than the one derived from change in the parameter value of the parameter type except $P_k$. The value of k is an integer equal to or larger than 1 and equal to or smaller than N.

For example, in the training data acquisition stage, the given object which contains the region of interest is continuously captured while changing the control information so that the image is acquired. In the foregoing circumstance, the parameter value is changed by each type. Assuming that the control information as indicated by C1 is set to an initial value, referring to C2, only the parameter value of $P_1$ is changed from $p_1$ to $p_1'$ as the initial value so that the image is acquired. This applies to the subsequent information hereinafter. The estimated probability is obtained by inputting the image acquired at each timing to the NN1 as described above. In an example of the case, the estimated probability is ranged from 0 to 100%.

Referring to the example of FIG. 9B, in the control information in the initial state, the estimated probability is as low as 40%. The control information is changed to modify property of the acquired image so that the estimated probability to be output upon input of such image to the NN1 is changed as well. For example, it is assumed that the estimated probability is maximized when changing the parameter value of the parameter type $P_k$ as indicated by C3 of FIG. 9B. In this case, the parameter type dominant over the estimated probability is $P_k$, and accordingly, it is conceivable that preferential change in the parameter type $P_k$ allows improvement of the estimated probability. That is, the acquisition section 410 sets the image of C1 to the second input image, the parameter values $p_1$ to $p_N$ of C1 to the control information, and the type $P_k$ to the priority parameter type to acquire a single set of training data. The data for acquiring the training data are not limited to those illustrated in FIG. 9B, but may be variously modified.

As FIG. 9C illustrates, the NN2 receives inputs of the second input image and the control information, and performs the arithmetic operation in the forward direction to output the probability that change in the parameter type is recommended. For example, the output layer of the NN2 includes N nodes, and outputs N sets of output data.

Figure 10:
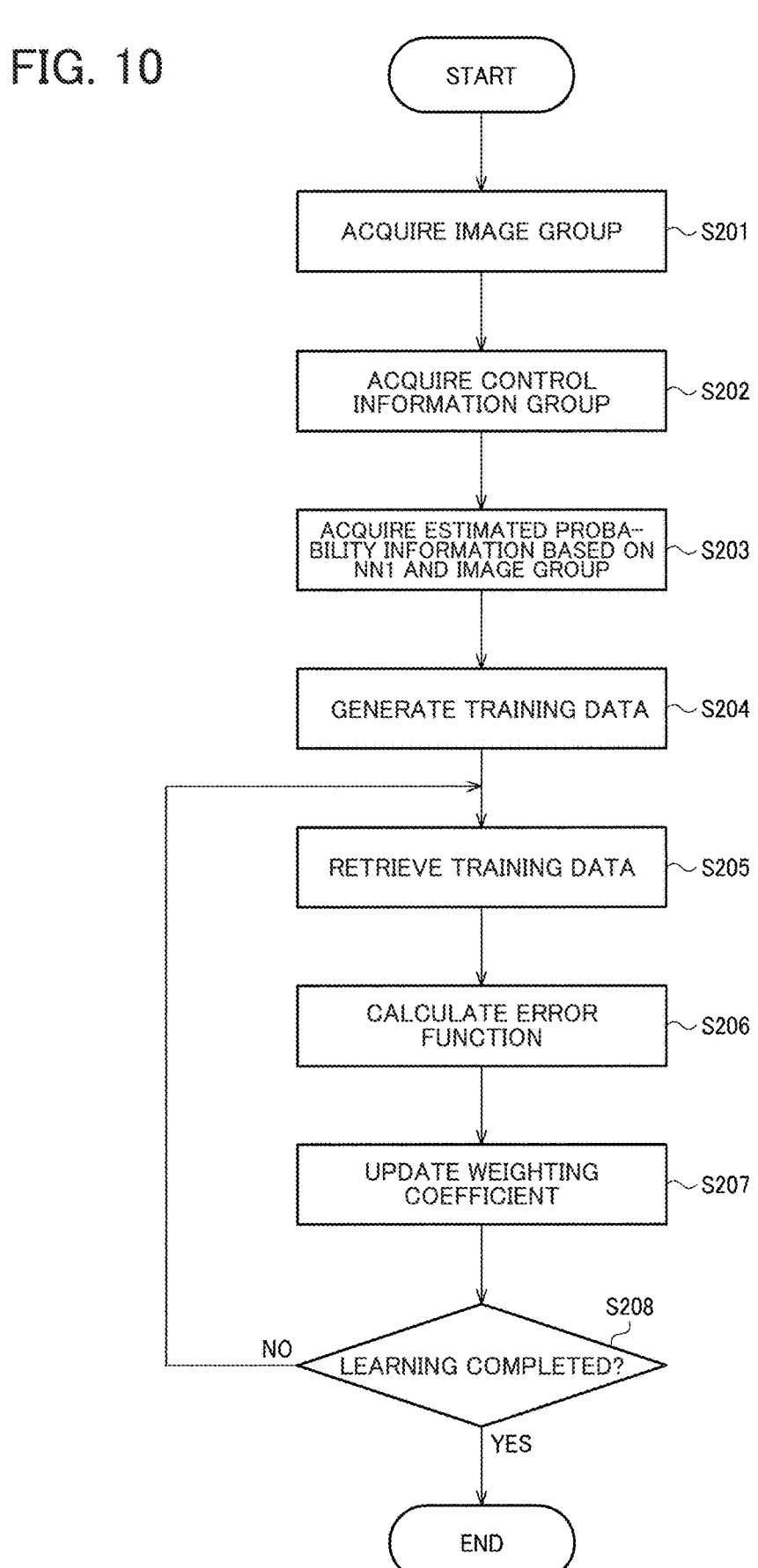
FIG. 10 illustrates a flowchart representing NN2 learning processing.

FIG. 10 is a flowchart illustrating learning processing of the NN2. First, in steps S201 and S202, the acquisition section 410 acquires an image group corresponding to the one illustrated in FIG. 9B, and a control information group as a set of control information upon acquisition of the images, respectively. In step S203, the acquisition section 410 inputs the respective images to the generated NN1 to acquire an estimated probability group. The data as illustrated in FIG. 9B are acquired by performing processing in steps S201 to S203.

Next, in step S204, the acquisition section 410 performs processing of acquiring the training data based on the data as illustrated in FIG. 9B. Specifically, the acquisition section 410 acquires a large volume of training data having the second input image, the control information, and the priority parameter type, correlated with one another, and stores those data.

In step S205, the acquisition section 410 retrieves one set of training data. In step S206, the learning section 420 obtains the error function. Specifically, the learning section 420 inputs the second input image and the control information of the training data to the NN2, and performs the arithmetic operation in the forward direction based on the corresponding weighting coefficient. For example, as FIG. 9C illustrates, N data are obtained as operation results, indicating the probability that each parameter type should be recommended as the priority parameter type. If the output layer of the NN2 is a known softmax layer, the N data are probability data having the sum total set to 1. If the priority parameter type included in the training data is $P_k$, the correct label is formed as the data having the probability of recommending change in $P_1$ to $P_{k-1}$ set to 0, the probability of recommending change in $P_k$ set to 1, and the probability of recommending $P_{k+1}$ to $P_N$ set to 0. The learning section 420 obtains the error function based on comparison between N probability data obtained through the arithmetic operation in the forward direction and N probability data each as the correct label.

In step S207, the learning section 420 performs processing of updating the weighting coefficient to make the error function small. As described above, the error back propagation method or the like may be used for performing the processing in step S207. In step S208, the learning section 420 determines whether or not learning processing is to be finished. The learning processing may be finished based on the number of times of updating the weighting coefficient as described above, or the accuracy rate of the estimation processing using the verification data. If No is obtained in step S208, the process returns to step S205 where the learning processing is continuously performed based on the subsequent training data. If Yes is obtained in step S208, the learning processing is finished. The learning device 400 transmits the information of the generated trained model to the processing system 100.

The processing performed by the learning device 400 of the present embodiment may be implemented as the learning method. The learning method of the present embodiment allows generation of the trained model by performing the processing of acquiring an image captured by the endoscope apparatus as the input image, acquiring the control information for obtaining the input image when using information for controlling the endoscope apparatus as control information, acquiring the control information for improving the estimated probability information which represents the probability of the region of interest detected from the input image, and performing machine learning of a relationship among the input image, the control information for obtaining the input image, and the control information for improving the estimated probability information. The control information for improving the estimated probability information herein may be the priority parameter type as described above, a combination of the priority parameter type and the specific parameter value as a modification to be described later, or a set of multiple parameter types and parameter values for the respective parameter types as further modification to be described later.

2.2 Inference Processing

Figure 11:
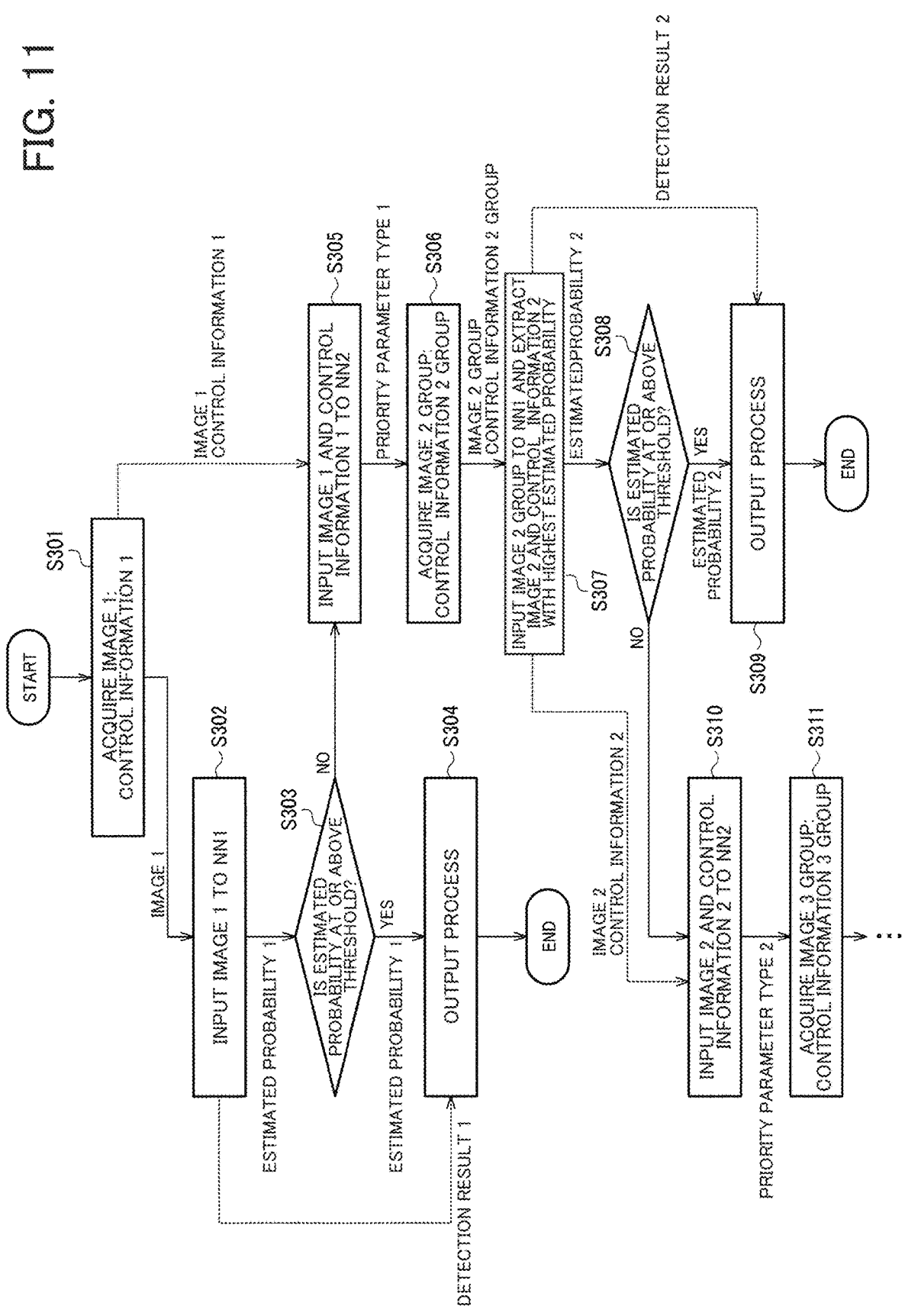
FIG. 11 illustrates a flowchart representing detection processing and control information identifying processing.

FIG. 11 is a flowchart illustrating processing to be performed by the processing system 100 of the present embodiment. First, in step S301, the acquisition section 110 acquires a detection target image. For example, the acquisition section 110 may be configured to acquire the detection target image once every two frames as described later referring to FIG. 12. The acquisition section 110 is capable of acquiring the control information used for acquiring the detection target image from the control section 130.

In step S302, the processing section 120 (detection processing section 334) inputs the detection target image to the NN1 to obtain a detection result of the region of interest, and the estimated probability representing its probability through an arithmetic operation. In step S303, the processing section 120 determines whether or not the estimated probability is equal to or higher than a given threshold. If Yes is obtained in step S303, the detection result of the region of interest is considered as being sufficiently reliable. The process then proceeds to step S304 where the processing section 120 outputs the detection result of region of interest. For example, the detection result of the region of interest derived from the detection processing section 334 is transmitted to the post-processing section 336 for post-processing. Thereafter, the result is displayed on the display section 340. As described later referring to FIG. 13A and FIG. 13B, the processing section 120 outputs the estimated probability together with the detection result of region of interest.

If No is obtained in step S303, the detection result of region of interest is considered as having low reliability. Display of such result may be non-beneficial for user's diagnosis and the like. Meanwhile, omission of the display itself may fail to notify the user of possibility that the region of interest exists. For this reason, in the present embodiment, the control information is changed.

If No is obtained in step S303, the process proceeds to step S305 where the processing section 120 (control information identifying section 335) performs processing of updating the control information. The processing section 120 inputs the detection target image acquired in step S301, and the control information to the NN2 so that the priority parameter type is identified.

In step S306, the control section 130 (control section 332) performs control for changing the parameter value of the priority parameter type. The acquisition section 110 acquires the detection target image based on the changed control information. In this case, the NN2 identifies the priority parameter type, but does not identify the specific parameter value. Accordingly, the control section 332 performs control for sequentially changing the parameter value of the priority parameter type. The acquisition section 410 acquires the detection target image group based on the parameter value group.

In step S307, the processing section 120 inputs the respective detection target images of the detection target image group to the NN1 to obtain the detection result of the region of interest, and the estimated probability indicating probability of the result. The detection processing section 334 extracts the parameter value with the highest estimated probability, and the detection target image from the parameter value group and the detection target image group, respectively.

In step S308, the detection processing section 334 determines whether or not the estimated probability of the region of interest in the extracted detection target image is equal to or higher than the given threshold. If Yes is obtained in step S308, the detection result of the region of interest is considered to be highly reliable. Accordingly, in step S309, the detection processing section 334 outputs the detection result of the region of interest.

If No is obtained in step S308, the process proceeds to step S310 where the control information identifying section 335 performs processing of updating the control information. The control information identifying section 335 inputs the detection target image extracted in step S307, and the control information used for acquiring the detection target image to the NN2 so that the priority parameter type is determined.

The priority parameter type determined in step S310 may be the parameter type $P_j$ (j is an integer that satisfies $j{\neq}i$) which is different from the priority parameter type $P_i$ determined in step S305. The processing in step S310 may be performed in the case where the estimated probability is not sufficiently improved in spite of adjustment of the parameter type $P_i$. The parameter type different from the parameter type $P_i$ is set to the next priority parameter type to allow efficient improvement of the estimated probability. In step S311, the acquisition section 410 acquires the detection target image group based on the parameter value group in the control for sequentially changing the parameter value of the priority parameter type.

In step S310, the processing result obtained in step S305 may be utilized by omitting the processing using the NN2. For example, the control information identifying section 335 may be configured to select the parameter type determined in step S305 that it should be recommended with the second priority as the priority parameter type.

Referring to FIG. 11, the explanation has been made by developing the loop processing for clarifying changes in the detection target image, the control information upon acquisition of the detection target image, and the priority parameter type. As described with respect to the processing in steps S301 to S305, the loop processing including such processing as acquisition of the detection target image and the control information, detection, determination of the estimated probability using the threshold, and identification of the control information is performed repeatedly until establishment of the condition that the estimated probability is equal to or higher than the threshold. In step S311 onward, the similar loop is continuously performed. In the case where even continuously performing the loop fails to sufficiently improve the estimated probability, the processing section 120 finishes the processing when, for example, all the parameter types have been changed, or the loop processing has been performed the predetermined number of times.

Figure 15:
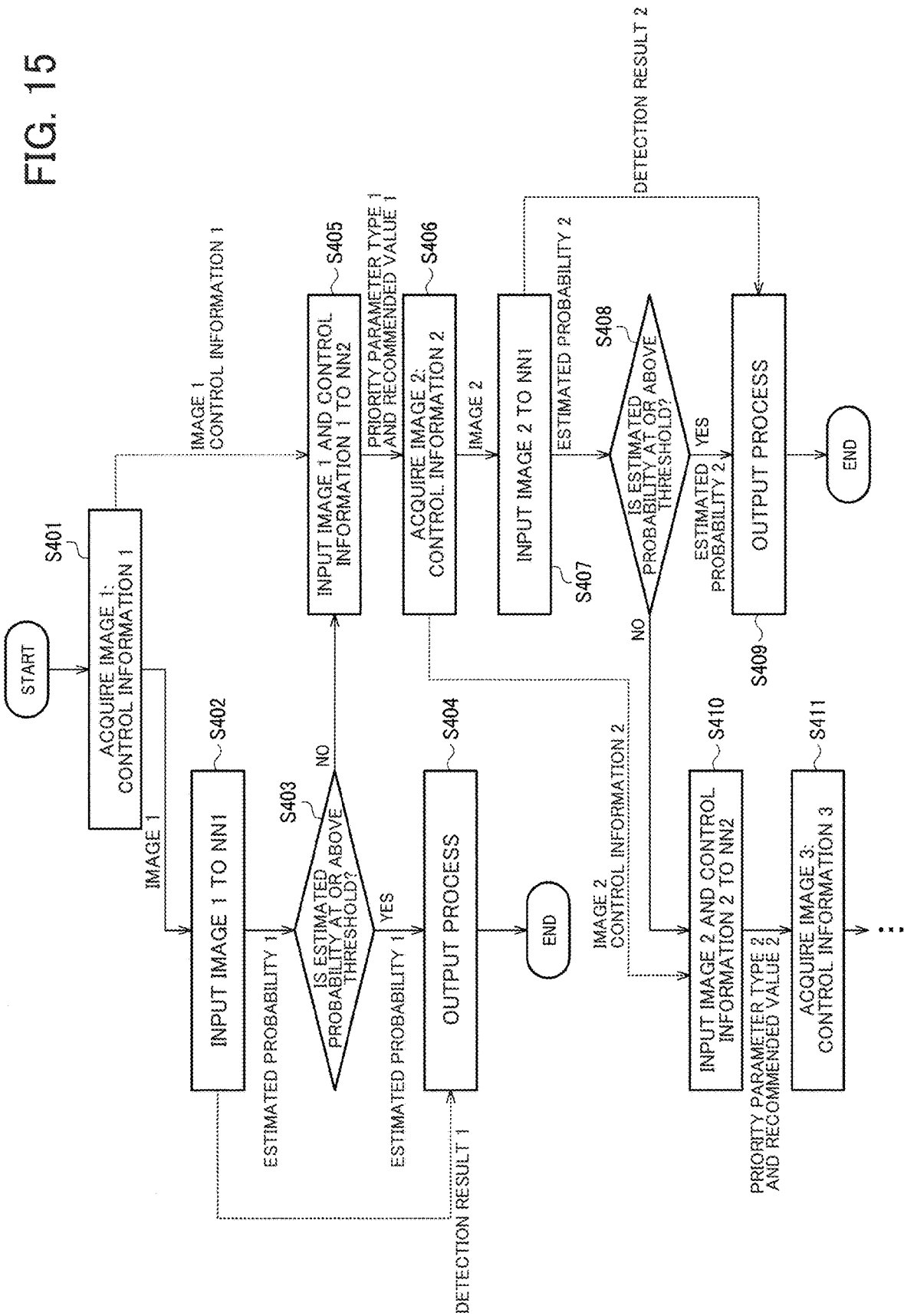
FIG. 15 illustrates a flowchart representing detection processing and control information identifying processing.

The processing which has been described referring to FIG. 11 focuses on the single region of interest. It cannot be said that it is preferable to continuously perform the processing to the single detected region of interest the excessive number of times for the following reasons. That is, as the visual field of the imaging section varies depending on the operation condition of the insertion section 310*b*, it is presumed that the region of interest deviates from the detection target image, and a region of interest is newly detected in the detection target image. As described above, the maximum number of implementation of the loop processing is limited to allow smooth switching from the processing to the given region of interest to the processing to the different region of interest. Especially, as illustrated in FIG. 11 and FIG. 15 to be referred later, the number of the parameter types to be changed is small, which may need substantial time for improving the estimated probability. Accordingly, it is essential to suppress the number of loops.

As described above, the processing section 120 of the processing system 100 is operated in accordance with the trained model to detect the region of interest included in the detection target image, and to calculate the estimated probability information related to the detected region of interest. The trained model herein corresponds to the NN1. The processing section 120 may be configured to be operated in accordance with the trained model so that the control information for improving the estimated probability is identified.

The arithmetic operation performed by the processing section 120 in accordance with the trained model, that is, the one for outputting the output data based on the input data may be implemented either by software or hardware. In other words, software may be configured to perform a product-sum operation performed by each node in FIG. 6A, and the filter processing performed in the convolutional layer of the CNN. Alternatively, the arithmetic operation may be performed by the circuit device such as FPGA, or combination of software and hardware. Consequently, the operation of the processing section 120 in accordance with the instruction from the trained model may be performed in various forms. For example, the trained model includes an inference algorithm and the weighting coefficient used for the inference algorithm. The inference algorithm is used for filter arithmetic operation or the like based on the input data. In this case, the inference algorithm and the weighting coefficient both stored in the storage section may be retrieved by the processing section 120 to allow implementation of the software-based inference processing. The storage section is exemplified by the storage section 333 of the processing device 330. However, other type of storage section may be used. Alternatively, the inference algorithm may be implemented by the FPGA or the like so that the weighting coefficient is stored in the storage section. The inference algorithm including the weighting coefficient may also be implemented by the FPGA or the like. In this case, the storage section for storing the trained model information is exemplified by an internal memory of the FPGA.

The processing section 120 calculates first estimated probability information based on the first detection target image derived from the control using the first control information, and the trained model. If it is determined that probability represented by the first estimated probability information is lower than the given threshold, the processing section 120 performs processing of identifying the second control information as the one for improving the estimated probability information. The processing corresponds to those performed in steps S302, S303, and S305 in FIG. 11, for example.

This makes it possible to attempt acquisition of more reliable information in the case of insufficient estimated probability, that is, low reliability of the detected region of interest.

Provision of the information with low estimated probability to the user, which has been practiced in the generally employed method, may cause the risk of erroneous diagnosis by the user. Meanwhile, in the case where a high threshold of the estimated probability is set as a reference for determining whether such information is provided to the user, the user's erroneous diagnosis may be suppressed. However, the support information volume to be provided is reduced, leading to increase in lesion oversight errors. The method according to the present embodiment is capable of solving the above-described tradeoff problem. This makes it possible to attain highly accurate diagnosis by the user, and provision of information which suppresses the oversight error.

The processing section 120 may be configured to calculate second estimated probability information based on the second detection target image derived from the control using the second control information, and the trained model. If it is determined that probability represented by the second estimated probability information is lower than the given threshold, the processing section 120 performs processing of identifying the third control information as the one for improving the estimated probability information. The processing corresponds to those performed in steps S307, S308, and S310 in FIG. 11, for example.

This makes it possible to further change the control information in the case of insufficient estimated probability despite the change in the control information. It is therefore possible to improve probability of acquiring the highly reliable information, specifically, to search the appropriate control information broadly so that the estimated probability exceeds the given threshold.

As illustrated in FIG. 4, the control information includes at least one of the light source control information for controlling the light source 352 which irradiates the object with illumination light, the imaging control information for controlling the imaging condition based on which the detection target image is captured, and the image processing control information for controlling the image processing to the signal of the captured image. As described above, the detection target image is acquired by performing the steps of allowing the light source 352 to emit light, allowing the image sensor 312 to receive light from the object, and processing the image signal as the light reception result. Performing the control related to any one of those steps allows change in the property of the detection target image to be acquired. This makes it possible to adjust the estimated probability. As described above, however, the control section 130 does not have to control all of the light source, imaging, and image processing for improving the estimated probability. It is possible to omit controlling one or two of those processing operations.

The control information may be the information indicating at least one of properties including the color tone, brightness, and the position of the region of interest in the image. In other words, the light source 352 or the like may be controlled so that at least one of the color tone, brightness, and the position of the region of interest in the detection target image approximates the desired value. The estimated probability may be improved by, for example, making the color tone of the region of interest resemble the color tone of the input image included in the training data, in a narrow sense, making the color tone resemble the color tone of the part corresponding to the region of interest in the input image. Alternatively, the estimated probability may be improved by controlling the light source 352 so that brightness of the region of interest in the detection target image is made optimum for the region of interest.

The control information may be configured to include the first to the Nth (N is an integer equal to or larger than 2) parameter types. The processing section 120 may be configured to identify the second control information by changing the parameter type to the ith (i is an integer which satisfies $1 \leq i \leq N$) parameter type among the first to the Nth parameter types included in the first control information. This makes it possible to change the parameter type to the one with higher degree of contribution to the estimated probability, and further to improve the estimated probability by performing the efficient control. As described later, such control is performed more easily than the control for simultaneously changing parameter values of multiple parameter types.

The processing section 120 calculates the second estimated probability information based on the second captured image derived from the control using the second control information, and the trained model. The processing section 120 may be configured to identify the third control information by changing the parameter type to the jth (j is an integer which satisfies $1 \leq j \leq N$, $j \neq i$) parameter type among the first to the Nth parameter types included in the second control information when it is determined that probability represented by the second estimated probability information is lower than the given threshold.

This allows an attempt to change the parameter value of the different parameter type when the change in the parameter value of the given parameter type has failed to sufficiently improve the estimated probability. Accordingly, the probability of improving the estimated probability may be increased.

The processing section 120 may be configured to perform processing of identifying the second control information as the one for improving the estimated probability information based on the first control information and the first detection target image. That is, when identifying the control information, it is possible to use not only the detection target image but also the control information for acquiring such detection target image. For example, as illustrated in FIG. 9C, the NN2 as the trained model for identifying the control information receives an input of a set of the image and the control information.

The foregoing configuration allows the processing to be performed in consideration not only of the detection target image but also the condition by which such detection target image has been acquired. The resultant processing accuracy may be further improved than the case of inputting only the detection target image. However, the processing of identifying the second control information does not necessarily require the use of the first control information. For example, the control information may be omitted from the training data as illustrated in FIG. 9A. In this case, the input operation for processing of identifying the control information becomes less frequent, and accordingly, the processing load may be reduced. As the training data volume is reduced, the learning processing load may also be reduced.

The processing section 120 may be configured to perform processing of identifying the control information for improving the estimated probability information based on the second trained model and the detection target image. The second trained model is acquired by machine learning with respect to the relationship between the second input image and the control information for improving the estimated probability information. The second trained model corresponds to the NN2 as described above.

It is therefore possible to utilize the machine learning for processing of identifying the control information as well as the detection processing. Accordingly, accuracy of identifying the control information is improved to increase the estimated probability to be equal to or higher than the threshold acceleratedly. However, as described later, the processing of identifying the control information may be modified as the processing without utilizing the machine learning.

The processing to be performed by the processing system 100 of the present embodiment may be implemented as the image processing method. The image processing method of the present embodiment is implemented by acquiring the detection target image captured by the endoscope apparatus, detecting the region of interest included in the detection target image based on the trained model acquired by machine learning for calculating the estimated probability information representing probability of the region of interest in the input image, and the detection target image, calculating the estimated probability information related to the detected region of interest, and identifying the control information for improving the estimated probability information related to the region of interest in the detection target image based on the detection target image on the assumption that the information used for controlling the endoscope apparatus is set as the control information.

2.3 Background Processing and Display Processing

Figure 12:
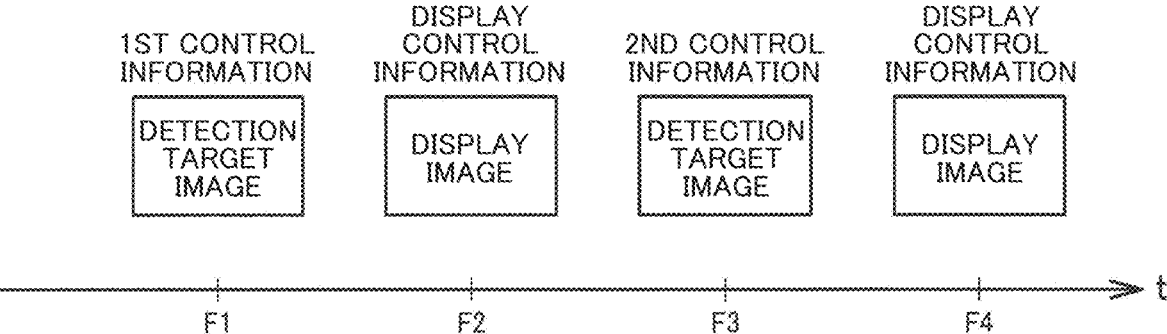
FIG. 12 illustrates an example of display images and timing for acquiring a detection target image.

FIG. 12 illustrates a relationship between the imaging frame and an image acquired in each frame. For example, the acquisition section 110 of the processing system 100 detects the region of interest and acquires the detection target image as the target for calculating the estimated probability information in the given frame. The acquisition section 110 acquires the display image used for display on the display section 340 in the frame different from the given frame.

That is, the method according to the present embodiment may be configured to separate the detection target image as the target for processing of detection and control information identification performed by the processing system 100 from the display image to be displayed for the user. This makes it possible to manage the control information utilized for acquiring the detection target image and the display control information for acquiring the display image separately.

As described above, the property of the image to be acquired is changed by modifying the control information. Frequent or rapid change in the control information of the display image makes the change in the image greater. This may cause the risk of interference with the user's observation and diagnosis. Separating the detection target image from the display image may suppress the rapid change in the control information for display image. That is, the display image property may be changed by the user himself. Even in the case of automatic change in the property, such change can be suppressed in a gradual manner. This may suppress interference with the user's diagnosis.

It is possible not to display the detection target image so that the control information may be rapidly changed. Accordingly, the control for improving the estimated probability may be performed acceleratedly. In the case where light quantity of the LED as the light source 352 is adjusted in the generally employed automatic dimming control, the resultant light quantity change becomes gradual in a restricted manner compared with the light quantity change normally attained as the property of LED. Such control is performed for avoiding rapid brightness change which may cause the risk of interference with the user's diagnosis. The light quantity change of the detection target image hardly causes the problem despite the rapid change. The LED is allowed to fully exhibit its light quantity changing capability.

The acquisition section 110 may be configured to acquire the detection target image and the display image alternately as illustrated in FIG. 12. This makes it possible to reduce the difference between the timing for acquiring the detection target image and the timing for acquiring the display image.

The processing section 120 of the processing system 100 may be configured to display the detection result of the region of interest detected based on the detection target image, and the estimated probability information calculated based on the detection target image when the estimated probability information calculated based on the trained model (NN1) and the detection target image is equal to or higher than the given threshold.

Figure 13A:
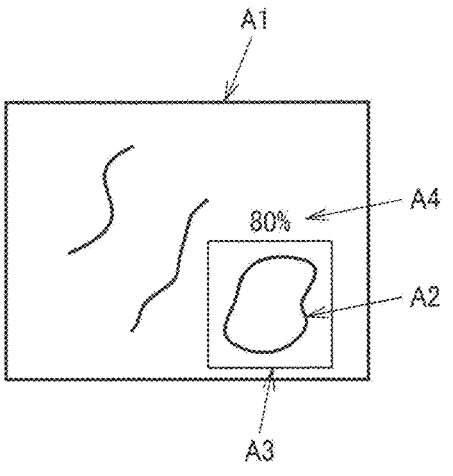
FIGS. 13A and 13B each illustrate a display screen example.
Figure 13B:
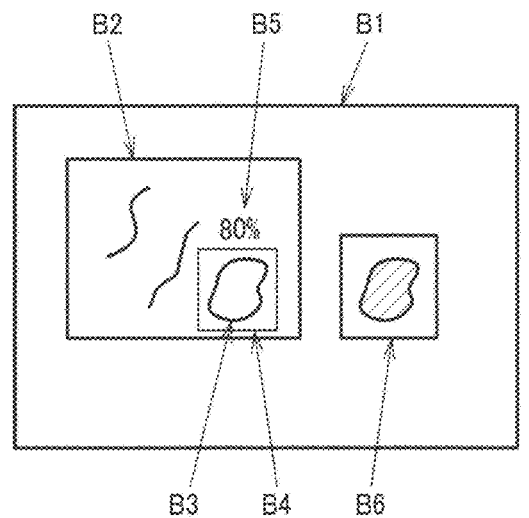

FIG. 13A and FIG. 13B illustrate an example of the display image on the display section 340. Referring to FIG. 13A, a reference code A1 denotes a display image on the display section 340. A reference code A2 denotes the region of interest captured as the display image. A reference code A3 denotes a detection frame detected on the detection target image. A reference code A4 denotes an estimated probability. As FIG. 13A illustrates, the detection result of the region of interest and the estimated probability information are superposed on the display image and displayed to provide the user with the information related to the region of interest in the display image comprehensively.

For example, the detection target image in this case has been acquired in the frame F3 as illustrated in FIG. 12, and the display image has been acquired in the frame F4. This makes it possible to reduce the difference in the timing of imaging between the detection target image and the display image. As the difference between the condition of the region of interest in the detection target image and the condition of the region of interest in the display image is reduced, the detection result based on the detection target image may be easily correlated with the display image. For example, the difference in the position/size of the region of interest between the detection target image and the display image is sufficiently reduced. The probability that the region of interest on the display image is included in the detection frame may be raised when superposing the detection frame. The display image and the detection target image herein are not limited to those images acquired in the consecutive frames. For example, depending on the time required for performing the detection processing, it is possible to superpose and display the detection result using the detection target image in the frame F3 on the display image acquired in the timing behind the frame F4, for example, a not shown frame F6 or F8.

The processing section 120 may be configured to perform processing of displaying the region which includes at least the region of interest of the detection target image, and the display image, which are correlated with each other when the estimated probability information calculated based on the trained model NN1 and the detection target image is equal to or higher than the given threshold.

For example, as FIG. 13B illustrates, the processing section 120 may be configured to perform processing of displaying a part of the detection target image on the display section 340. Referring to FIG. 13B, a reference code B1 denotes a display region of the display section 340. Similar to the reference codes A1 to A4 in FIG. 13A, reference codes B2 to B5 denote the display image, the region of interest in the display image, the detection frame, and the estimated probability, respectively. The processing section 120 may be configured to display a part of the detection target image in a part of the display region, which is different from the one having the display image displayed thereon as indicated by B6.

The detection target image having the region of interest with high estimated probability is regarded as the image which allows the user to easily identify the region of interest. Accordingly, display of a part of the detection target image which includes at least the region of interest enables to support the determination as to whether the region indicated by the detection frame is truly the region of interest. FIG. 13B illustrates an example of partially displaying the detection target image. However, an entire detection target image may be displayed in a non-restrictive manner.

3. Modification

Several modifications will be described hereinafter.

3.1 Configuration of Trained Model

The explanation has been made with respect to an example that the NN1 as the trained model for detection processing, and the trained model NN2 for processing of identifying the control information are separated from each other. The NN1 and the NN2 may be implemented by a single trained model NN3.

For example, the NN3 is a network which receives inputs of the detection target image and the control information, and outputs the detection result of the region of interest, the estimated probability information, and the priority parameter type. Various specific configurations of the NN3 are conceivable. For example, the NN3 may be configured as a model including a feature amount extraction layer sharedly used for the detection processing and processing of identifying the control information, a detection layer for performing the detection processing, and a control information identifying layer for performing processing of identifying the control information. The feature amount extraction layer receives inputs of the detection target image and the control information, and outputs the feature amount. The detection layer receives an input of the feature amount from the feature amount extraction layer, and outputs the detection result of the region of interest and the estimated probability information. The control information identifying layer receives an input of the feature amount from the feature amount extraction layer, and outputs the priority parameter type. For example, based on the training data illustrated in FIG. 7A, the weighting coefficient included in the feature amount extraction layer and the detection layer is learned. Based on the training data as illustrated in FIG. 9A, the weighting coefficient included in the feature amount extraction layer and the control information identifying layer is learned. Depending on the training data format, the detection layer and the control information identifying layer may be targeted for learning simultaneously.

3.2 Modified Example Related to Processing of Identifying Control Information

Modified Example 1 of NN2

FIG. 14A illustrates another example of training data for generating a trained model used for the processing of identifying the control information. FIG. 14B illustrates an example of data for generating the training data as illustrated in FIG. 14A. FIG. 14C illustrates an input/output operation of the NN2.

As FIG. 14A illustrates, the training data include the second input image, the control information used for acquiring the second input image, the priority parameter type, and a recommended value for the priority parameter type. The control information is the same as the one in the example illustrated in FIG. 9A, including the parameter values $p_1$ to $p_N$ of the parameter types $P_1$ to $P_N$, respectively. The priority parameter type $P_k$ which is the same as the one illustrated in FIG. 9A indicates the information for identifying any one of the parameter types. The recommended value $p_k{}'$ is the value recommended for the parameter value of the parameter type $P_k$.

For example, in the training data acquisition stage, a given object which contains the region of interest is sequentially captured while changing the control information so that the image is acquired. In such a case, data related to multiple kinds of parameter values for a given parameter type are acquired. An explanation will be made with respect to an example that M candidates are set for each of the parameter values $p_1$ to $p_N$ so that the description is simplified. The parameter value $p_1$ is selectable from M kinds of candidate values of $p_{11}$ to $p_{1M}$. This applies to the parameter values $p_2$ to $p_N$. The number of candidates for the parameter value may be made different in accordance with the parameter type.

It is assumed that initial value of the parameter value is set to $p_{11}, p_{21}, \ldots, p_{N1}$ as indicated by D1. As for data in the range indicated by D2, the parameter value of the parameter type $P_1$ is only changed to $p_{12}$ to $p_{1M}$ sequentially, and the parameter values of the parameter types $P_2$ to $P_N$ are fixed. Similarly, in the range indicated by D3, the parameter value of the parameter type $P_2$ is only changed to $p_{22}$ to $p_{2M}$ sequentially, and parameter values of other parameter types are fixed. This applies to subsequent data hereinafter. In the example as illustrated in FIG. 14B, each parameter value of the N parameter types is changed in M−1 ways from the initial state indicated by D1. Based on the N×(M−1) different control information data, N×(M−1) pieces of images are acquired. The acquisition section 410 obtains the estimated probability by inputting each of the N×(M−1) images to the NN1.

It is assumed that the estimated probability is maximized as a result of changing the parameter value $p_k$ of the parameter type $P_k$ to $p_k{}'$ as one of values from $p_{k2}$ to $p_{kM}$. In such a case, the acquisition section 410 sets the image indicated by D1 to the second input image, the parameter values $p_{11}$ to $p_{N1}$ indicated by D1 to the control information, the parameter type $P_k$ to the priority parameter type, and the value $p_k{}'$ to the recommended value so that the single set of training data are acquired. The data for acquiring the training data are not limited to those illustrated in FIG. 14B, but may be variously modified. It is not necessary to acquire all the N×(M−1) additional data, for example. The modification may be configured to omit a part of those data in consideration of the processing load.

As FIG. 14C illustrates, the NN2 receives inputs of the second input image and the control information, and performs an arithmetic operation in the forward direction to output the priority parameter type and the recommended value.

For example, the output layer of the NN2 may be configured to include N×M nodes, and output N×M output data. The N×M output nodes include M nodes for outputting probability data required to set the $P_1$ to $p_{11}$, $P_1$ to $p_{12}, \ldots$, and $P_1$ to $p_{1M}$, respectively. Similarly, the output nodes include M nodes for outputting probability data required to set $P_2$ to $p_{21}$, $P_2$ to $p_{22}, \ldots$, and $P_2$ to $p_{2M}$, respectively. This applies to subsequent data hereinafter. The NN2 according to the present modification outputs recommended probability data with respect to all the combinations of the N kinds of priority parameter types and M kinds of parameter values. If the node which allows the probability data to be maximized is determined, the priority parameter type and the recommended value may be identified. The specific configuration of the NN2 is not limited to the one as described above, but may be configured in another way for allowing identification of the priority parameter type and the recommended value.

The flow of NN2 learning processing is similar to the one as illustrated in FIG. 10. In step S206 of the flow, the learning section 420 inputs the second input image and the control information of the training data to the NN2, and performs an arithmetic operation in the forward direction based on the corresponding weighting coefficient so that N×M probability data are obtained. The learning section 420 then obtains the error function by comparing the N×M probability data with the priority parameter type/recommended value of the training data. For example, in the case where the priority parameter type included in the training data is $P_1$, and the recommended value is $p_{11}$, the correct label informs that the probability data for setting the $P_1$ to $p_{11}$ becomes 1, and all other probability data become 0.

FIG. 15 is a flowchart illustrating processing to be performed by the processing system 100 of the present embodiment. Steps S401 to S404 correspond to steps S301 to S304 of FIG. 11. That is, the processing section 120 obtains the estimated probability by inputting the detection target image to the NN1. If the estimated probability is equal to or higher than the threshold, the output processing is performed, otherwise the control information is changed.

If No is obtained in step S403, the process proceeds to step S405 where the processing section 120 (control information identifying section 335) performs processing of updating the control information. The processing section 120 inputs the detection target image acquired in step S401, and the control information to the NN2 to determine the priority parameter. As described above referring to FIG. 14C, in the present modification, the parameter value to be recommended may be determined as well as the priority parameter type.

In step S406, the control section 130 (control section 332) performs the control for changing the parameter value of the priority parameter type to the recommended value. The acquisition section 110 acquires a detection target image based on the determined control information. Unlike the example as illustrated in FIG. 11, as the recommended value is identified, the control for sequentially changing the parameter value of the priority parameter type does not have to be performed. This makes it possible to improve estimated probability in a shorter time than the example in FIG. 11. As processing flow from steps S407 to S411 will be performed with repetition in the similar manner to the one as described above, explanations of those steps will be omitted.

<Modification 2 of NN2>

Figures 16A, 16B:
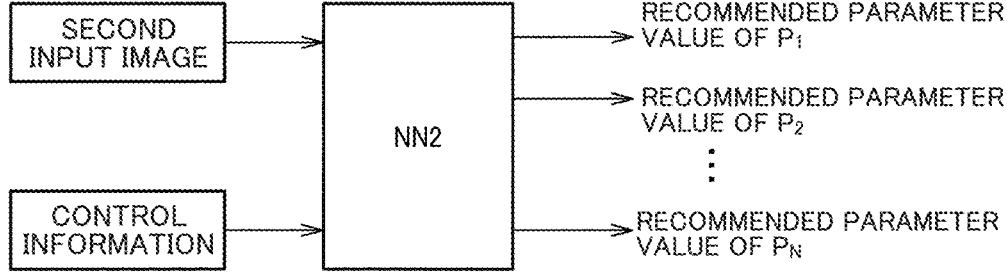
FIG. 16A illustrates a training data example for NN2.
FIG. 16B illustrates an example of input/output operation of NN2.

FIG. 16A illustrates another example of the training data for generating the trained model used for processing of identifying the control information. FIG. 16B illustrates an input/output operation of the NN2.

As illustrated in FIG. 16A, the training data include the second input image, the control information used for acquiring the second input image, and the recommended control information. The control information contains the parameter values $p_1$ to $p_N$ of the parameter types $P_1$ to $P_N$, respectively similar to the example as illustrated in FIG. 9A. The recommended control information contains parameter values $p_1'$ to $p_N'$ of the parameter types $P_1$ to $P_N$, respectively, which are recommended for improving the estimated probability.

For example, in the training data acquisition stage, a given object which contains the region of interest is continuously captured while changing the control information so that the image is acquired. In such a case, parameter values are changeable in M−1 ways for each of N kinds of parameter types. Accordingly, $(M-1)^N$ data as a result of all combinations are acquired. The acquisition section 410 sets the control information which maximizes the estimated probability to the recommended control information to acquire a single set of training data. Depending on values of N and M, a large number of images have to be captured for acquiring the training data. The collection target data may be limited to a part of the $(M-1)^N$ data. The data to be collected for acquiring the training data as illustrated in FIG. 16A may be variously modified.

As illustrated in FIG. 16B, the NN2 receives inputs of the second input image and the control information, and performs an arithmetic operation in the forward direction to output the recommended value for each parameter value of the respective parameter types. For example, the output layer of the NN2 includes N nodes, and outputs N output data.

The flow of NN2 learning processing is similar to the one as illustrated in FIG. 10. In step S206 of the flow, the learning section 420 inputs the second input image and the control information of the training data to the NN2, and performs an arithmetic operation in the forward direction based on the corresponding weighting coefficient so that N recommended values are obtained. The learning section 420 then obtains the error function by comparing the N recommended values with N parameter values included in the recommended control information of the training data.

Figure 17:
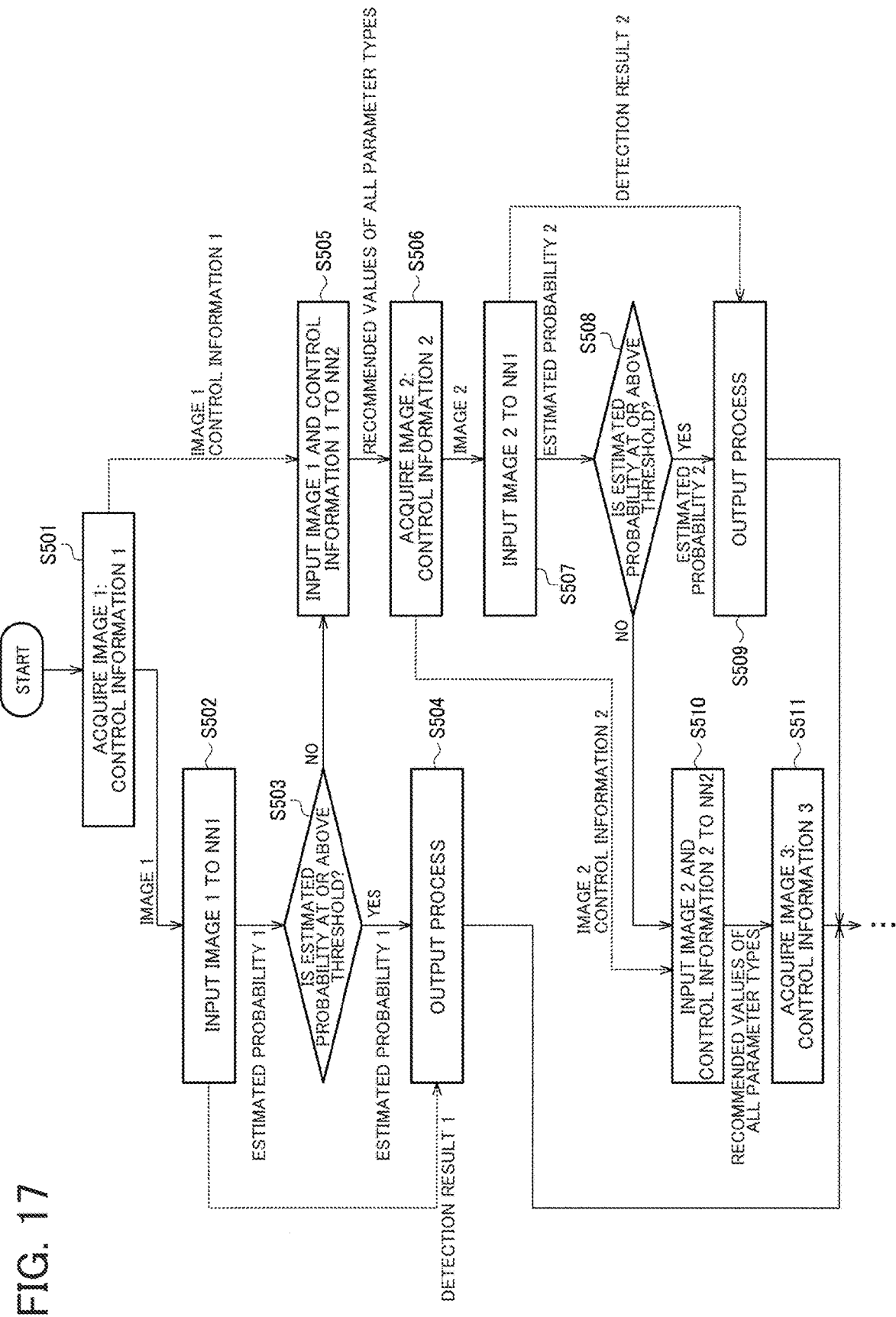
FIG. 17 illustrates a flowchart representing detection processing and control information identifying processing.

FIG. 17 is a flowchart illustrating processing to be performed by the processing system 100 of the present embodiment. Steps S501 to S504 correspond to steps S301 to S304 of FIG. 11. That is, the processing section 120 obtains the estimated probability by inputting the detection target image to the NN1. If the estimated probability is equal to or higher than the threshold, the display processing is performed, otherwise the control information is changed.

If No is obtained in step S503, the process proceeds to step S505 where the processing section 120 (control information identifying section 335) performs processing of updating the control information. The processing section 120 inputs the detection target image acquired in step S501, and the control information to the NN2 to determine the recommended control information. As described above, the control information herein is a set of recommended parameter values of the respective parameter types.

In step S506, the control section 130 (control section 332) performs the control for changing the parameter values of multiple parameter types to the recommended values. The acquisition section 110 acquires a detection target image based on the determined control information. Unlike the examples as illustrated in FIG. 11 and FIG. 15, multiple parameter types may be changed simultaneously. As illustrated in FIG. 17, in the present modification, the processing may not be finished upon implementation of the output processing (steps S504, S509), and the similar loop processing may be continuously performed.

As described above referring to FIGS. 16A and 16B, and FIG. 17, the control information contains the first to Nth (N is an integer equal to or larger than 2) parameter types. The processing section 120 may be configured to change two or more parameter types of the first to Nth parameter types which are included in the first control information so that the second control information is identified. Compared with the examples of FIG. 11 and FIG. 15, collective change in the parameter values of multiple parameter types in this way makes it possible to further improve the estimated probability in a short time.

<Modification without Utilizing Machine Learning>

An example has been described above with respect to application of machine learning to processing of identifying the control information. However, application of machine learning is not essential. For example, the processing section 120 may be configured to determine a priority order of multiple parameter types included in the control information, and change the control information according to the priority order. For example, in the processing flow as illustrated in the flowchart of FIG. 11, processing of changing the parameter value of the parameter type with the highest priority order is performed by omitting the processing in step S305.

Alternatively, the processing system 100 may be configured to store database in which the current image and control information are correlated with the priority parameter type for improving the estimated probability. The processing section 120 performs processing of obtaining similarity between the detection target image/control information obtained upon acquisition of the detection target image, and the image/control information stored in the database. The processing section 120 performs processing of identifying the control information by changing the priority parameter type correlated with the data with the highest similarity.

3.3 Operation Information

The acquisition section 110 of the processing system 100 may be configured to acquire operation information based on a user's operation of the endoscope apparatus. The processing section 120 identifies the control information for improving the estimated probability information based on the detection target image and the operation information. In other words, the operation information may be added as an input for the processing of identifying the control information.

For example, user's operations of depressing a magnification button, or bringing the leading end of the insertion section 310*b* close to the object are regarded as being intentionally performed by the user who desires to thoroughly examine the object. Supposedly, the user desires to obtain, for example, support information for supporting classification and discrimination of polyp rather than the one for merely informing existence/non-existence of the polyp. In such a case, the processing section 120 changes the illumination light to NBI, for example. This makes it possible to improve the estimated probability of the detection result of the region of interest, and in a narrow sense, to improve the estimated accuracy of the detection result including the classification result of the region of interest. That is, in response to a predetermined operation by the user, the processing section 120 identifies the control information based on the user's operation to allow implementation of the control reflecting the user's intention. User's operations such as magnification and approximation may cause the imaging section to confront the object. Accordingly, it is considered that the estimated probability may be improved by controlling light distribution as the control information.

It is possible to variously modify the specific parameter types and the parameter values of the control information to be identified based on the operation information.

For example, the storage section of the processing system 100 may be configured to store the trained model for processing of identifying the control information, specifically, the trained model NN2_1 upon implementation of user's operation, and the trained model NN2_2 upon non-implementation of user's operation. Based on the user's operation, the processing section 120 switches the trained model used for the processing of identifying the control information. For example, when detecting depression of the magnification button, the zoom button, or the like, the processing section 120 determines that the predetermined operation by the user has been performed, and switches the trained model. Alternatively, based on the illumination light quantity and the image brightness, the processing section 120 determines that the user's operation for bringing the insertion section 310*b* close to the object has been performed. For example, in the case of bright image despite small illumination light quantity, it may be determined that the leading end of the insertion section 310*b* has been brought close to the object.

For example, the NN2_1 is learned so that the parameter value of the NBI is likely to be selected as the parameter value related to the wavelength of the light source control information. This facilitates the detailed observation of the object using the NBI upon implementation of the user's operation. For example, the classification result in accordance with the NBI classification criteria is output as the detection result of the region of interest. For example, VS classification as a criterion for gastric lesion classification, or JNET, NICE classification, EC classification each as a criterion for colorectal lesion classification may be used for the NBI classification criteria.

Meanwhile, the NN2_2 is learned so that the parameter value of the normal light is likely to be selected as the parameter value related to the wavelength of the light source control information, for example. Alternatively, the NN2_2 may be formed as a model learned to raise the probability for identifying the control information which allows the light source device 350 to emit amber light and purple light. The amber light has a peak wavelength in the wavelength range from 586 nm to 615 nm. The purple light has a peak wavelength in the wavelength range from 400 nm to 440 nm. The above-described light of both types is narrowband light having half bandwidth of several tens of nm, for example. The purple light is suitable for acquiring the characteristic of a mucous membrane surface blood vessel or the gland duct structure. The amber light is suitable for acquiring the characteristic of a deep blood vessel of membrane, redding, inflammation, or the like. Emission of the amber light and the purple light allows detection of the region of interest, for example, the lesion detectable based on the characteristic of mucous membrane surface blood vessel or gland duct structure, or the lesion detectable based on the characteristic of mucous membrane deep blood vessel, redding, inflammation or the like. The purple light and the amber light are likely to be used upon non-implementation of the user's operation. This makes it possible to improve the estimated probability with respect to broadly ranged lesion such as cancer and inflammatory disease.

The configuration which differentiates the control information that is identified based on the operation information is not limited to the one for switching the trained model used for the identifying processing. For example, the NN2 is the model sharedly used upon implementation and non-implementation of the user's operation. Accordingly, the operation information may be used as an input to the NN2.

3.4 Switching of Trained Model for Detection Processing

The processing section 120 may be configured to perform the first processing for detecting the region of interest included in the detection target image based on the first trained model and the detection target image, and the second processing for detecting the region of interest included in the detection target image based on the second trained model and the detection target image. In other words, multiple trained models NN1 for detection processing may be provided. The first trained model is referred to as NN1_1, and the second trained model is referred to as NN1_2 hereinafter.

The processing section 120 selects one of the multiple trained models including the first trained model NN1_1 and the second trained model NN1_2. Upon selection of the first trained model NN1_1, the processing section 120 performs the first processing based on the first trained model NN1_1 and the detection target image, and calculates the estimated probability information to perform processing of identifying the control information for improving the calculated estimated probability information. Upon selection of the second trained model NN1_2, the processing section 120 performs the second processing based on the second trained model NN1_2 and the detection target image, and calculates the estimated probability information to perform processing of identifying the control information for improving the calculated estimated probability information.

As described above, the trained model for the detection processing may be switched in accordance with circumstances. The processing of identifying the control information for improving the estimated probability information as the output of the first trained model may be the same as or different from the processing of identifying the control information for improving the estimated probability information as the output of the second trained model. For example, as described above, it is possible to use multiple trained models for the processing of identifying the control information. Explanations will be made below with respect to specific examples for switching the trained model.

For example, the processing section 120 may be configured to be operable in any one of multiple determination modes including an existence determination mode for determining existence/non-existence of the region of interest included in the detection target image based on the first trained model NN1_1 and the detection target image, and a qualitative determination mode for determining a state of the region of interest included in the detection target image based on the second trained model NN1_2 and the detection target image. This makes it possible to perform processing in which either determination of existence/non-existence of the region of interest or determination of the state of the region of interest is prioritized. For example, the processing section 120 switches the trained model to be used for detection processing depending on whether all lesions have been found, the stage of the found lesion is required to be accurately classified, or the like.

Specifically, the processing section 120 may be configured to determine whether or not the determination mode is shifted to the qualitative determination mode based on the detection result of the region of interest in the existence determination mode. For example, the processing section 120 determines to shift the determination mode to the qualitative determination mode in the case where the detected region of interest is large in size, the position of the region of interest is close to the center of the detection target image, the estimated probability is equal to or higher than the predetermined threshold, or the like in the existence determination mode.

If it is determined that the determination mode is shifted to the qualitative determination mode, the processing section 120 calculates the estimated probability information based on the second trained model NN1_2 and the detection target image, and identifies the control information for improving the calculated estimated probability information. In this case, the trained model adapted to the circumstance is selected, and accordingly, the detection result desired by the user may be obtained. Furthermore, identifying the control information allows the detection result to be highly reliable.

For example, the NN1_1 and NN1_2 are trained models each derived from learning using training data with different properties. For example, the first trained model NN1_1 is learned based on the training data in which a first learning image is correlated with the information for identifying existence/non-existence or position of the region of interest in the first learning image. The second trained model NN1_2 is learned based on the training data in which a second learning image is correlated with the information for identifying the state of the region of interest in the second learning image.

The correct labels of the training data are thus differentiated from one another to allow discrimination of characteristics between the NN1_1 and the NN1_2. It is therefore possible to generate, as the NN1_1, the model exclusive to the processing of determining whether or not the region of interest exists in the detection target image. It is also possible to generate, as the NN1_2, the model exclusive to the processing of determining the state of the region of interest of the detection target image, for example, determining the corresponding lesion classification criteria as described above.

The first learning image may be the image captured using white light. The second learning image may be the image captured using special light with wavelength band different from that of the white light, or the image captured in the state where the object is magnified in comparison with the first learning image. Among the training data, information to be input may be differentiated to allow discrimination of characteristics between the NN1_1 and the NN1_2. In consideration of such a case, upon transition from the existence determination mode to the qualitative determination mode, the processing section 120 may be configured to change the light source control information of the control information. Specifically, the processing section 120 performs the control for emitting the normal light as illumination light in the existence determination mode, and emitting the special light as illumination light in the qualitative determination mode. This makes it possible to link the operation for switching the trained model with change in the control information.

A trigger for the switching operation of the trained model is not limited to the result of detecting the region of interest in the existence determination mode. For example, the acquisition section 110 may be configured to acquire operation information based on the user's operation to the endoscope apparatus as described above, and the processing section 120 may be configured to perform process of selecting the trained model based on the operation information. This also makes it possible to select the appropriate trained model depending on the observation desired by the user.

An aspect based on which the trained model for detection processing is switched is not limited to the existence determination/qualitative determination. For example, the processing section 120 may be configured to select the first trained model if the imaging target is the first imaging target and to select the second trained model if the imaging target is the second imaging target, as a result of implementation of the process of identifying the imaging target captured as the detection target image. The imaging target herein is an internal organ to be captured, for example. For example, the processing section 120 selects the first trained model if a large intestine is captured, and selects the second trained model if a stomach is captured. The imaging target may be a fragmented part of the single internal organ. For example, the trained model may be selected in accordance with any one of the ascending colon, transverse colon, descending colon, and sigmoid colon. The imaging target may be discriminated by the classification other than the internal organ.

The detection processing is thus performed using the trained model which varies depending on the imaging target to allow improvement of the detection processing accuracy, that is, improvement of estimated probability. The desired estimated probability thus can be easily attained by the processing as illustrated in FIG. 11 and the like.

In the foregoing case, the first trained model is learned based on the training data in which the first learning image derived from capturing the first imaging target is correlated with the information for identifying the region of interest of the first learning image. The second trained model is learned based on the training data in which the second learning image derived from capturing the second imaging target is correlated with the information for identifying the region of interest of the second learning image. This makes it possible to generate the trained model exclusive to detection of the region of interest of each imaging target.

3.5 Request for Changing Position/Posture of Imaging Section

The explanation has been made above with respect to an example of performing the processing of identifying the control information for improving the estimated probability. However, the processing which is different from the identifying processing may be performed for improving the estimated probability.

For example, the processing section 120 may be configured to perform notifying processing which requests the user to change at least one of a position and a posture of the imaging section of the endoscope apparatus with respect to the region of interest when the probability represented by the estimated probability information is determined to be lower than the given threshold. The imaging section herein corresponds to the image sensor 312, for example. Change in the position/posture of the imaging section corresponds to change in the position/posture of the leading end of the insertion section 310b.

For example, it is assumed that the image sensor 312 captures the region of interest from a diagonal direction. Capturing from the diagonal direction represents, for example, the state where the difference between the optical axis direction of the objective optical system 311 and the normal direction of an object plane is equal to or larger than the predetermined threshold. In this case, the region of interest in the detection target image is deformed to reduce its size on the image, for example. In this case, the resolution of the region of interest is low, which may cause the risk of failing to attain sufficient improvement of the estimated probability despite change in the control information. For this reason, the processing section 120 instructs the user to make the imaging section and the object confront with each other. The instruction may be displayed on the display section 340, for example. A guide related to the moving direction and moving amount of the imaging section may be displayed. As a result, the resolution of the region of interest in the image may be raised to attain improvement of the estimated probability.

In the case of a long distance between the region of interest and the imaging section, the region of interest on the image has its size reduced and its color darkened. Similarly, in this case, a mere adjustment of the control information may cause the risk of failing to attain sufficient improvement of the estimated probability. Accordingly, the processing section 120 instructs the user to bring the imaging section close to the object.

In the circumstance as described above, the processing section 120 may be configured to perform notifying processing which requires to change the position/posture of the imaging section in response to a trigger that the estimated probability has failed to be equal to or higher than the threshold despite change in the control information. As a result, the control information is changed preferentially, so that the operation load to the user may be suppressed in the condition satisfied by the change. By enabling the request for changing the position/posture, the estimated probability may be improved even in the condition which cannot be satisfied by changing the control information.

The trigger of the notifying processing for requiring change in the position/posture is not limited to the one as described above. For example, the NN2 described above may be configured as the trained model to output the information which identifies the control information, and further the information which identifies whether change in the position/posture is requested.

3.6 Display Processing or Storage Processing

Under the condition that control information is sequentially changed to the first control information, the second control information, and the like, it is assumed that the estimated probability is lower than the threshold when using the first control information.

The processing section 120 may be configured to display the detection result of the region of interest based on the first detection target image, and skip the display of the first estimated probability information. The processing section 120 may be configured to calculate the second estimated probability information based on the second detection target image acquired in the control using the second control information, and the NN1. The processing section may further be configured to perform processing of displaying the detection result of the region of interest based on the second detection target image, and the second estimated probability information if the second estimated probability information is equal to or higher than the given threshold.

If the estimated probability is lower than the threshold when using the first control information and the second control information, but becomes equal to or higher than the threshold when using the third control information, the processing section 120 displays the detection result of the region of interest based on the second detection target image, and skips the display of the second estimated probability information. The processing section 120 may be configured to perform processing of displaying the detection result of the region of interest in the third detection target image acquired in the control using the third control information, and the third estimated probability information calculated based on the third detection target image.

In the present embodiment, the above-described method allows improvement of the estimated probability despite the low estimated probability in the given timing. For example, if the estimated probability is lower than the threshold, such estimated probability may become equal to or higher than the threshold in the future by changing the control information. The present embodiment allows display of the detection result of the region of interest even if the estimated probability is lower than the threshold. This makes it possible to suppress oversight error of the region of interest. As the loop processing for determining the control information is performed repeatedly, the estimated probability value changes over time. The user is supposed to make sure whether or not the displayed region of interest is sufficiently reliable, and less interested in the time-series change in the estimated probability. Accordingly, the processing section 120 displays, for example, only the detection frame with no estimated probability in the updating loop processing of the control information, and displays the estimated probability together with the detection frame when the estimated probability is equal to or higher than the threshold. This makes it possible to attain the display comprehensible to the user.

The method according to the present embodiment allows improvement of the estimated probability, whereas in the case where the original estimated probability is excessively low, the method may fail to make the estimated probability equal to or higher than the threshold despite change in the control information. Accordingly, the processing section 120 may be configured to set a second threshold smaller than the threshold. The processing section 120 displays only the detection frame if the estimated probability is equal to or higher than the second threshold, and lower than the threshold. If the estimated probability is equal to or higher than the threshold, the processing section 120 displays the detection frame and the estimated probability.

The explanation has been made above with respect to the example for displaying the detection result of the region of interest and the display image, which are correlated with each other. The processing to be performed if the estimated probability is equal to or higher than the threshold is not limited to the display processing as described above.

For example, if the estimated probability information calculated based on the trained model NN1 and the detection target image is equal to or higher than the given threshold, the processing section 120 may be configured to store the detection target image. This makes it possible to accumulate the image considered to contain the region of interest with high visibility. In the normal observation using the endoscope system 300, the still image is not stored unless the user depresses the shutter button with clear intention. In the foregoing circumstance, there may be the case where the image with captured region of interest such as lesion cannot be stored. The use of the method for storing the movie may cause the heavy load of retrieving the region of interest from a large number of images. Meanwhile, as the storage processing is performed on the condition that the estimated probability is equal to or higher than the threshold, the information related to the region of interest may be appropriately stored.

If the estimated probability information calculated based on the trained model NN1 and the detection target image is equal to or higher than the given threshold, the processing section 120 may be configured to store the displayed image corresponding to the detection target image. As a result, the image viewed by the user himself may also be the target of the storage processing.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. A processing system comprising:
a processor including hardware, wherein the processor is configured to:
  acquire a first detection target image generated based on a first control information;
  calculate a detection result of a region of interest and estimated probability of the detected result based on the first detection target image;
  determine whether or not the estimated probability is equal to or higher than a first threshold;
  output the detection result of the region of interest in a case where the estimated probability is equal to or higher than the first threshold; and
  perform update of the first control information in a case where the estimated probability is less than the first threshold,
wherein in performing the update of the first control information, the processor is configured to:
  identify a second control information and a third control information based on the first detection target image and the first control information;
  acquire a second detection target image based on the second control information;
  acquire a third detection target image based on the third control information;
  detect the region of interest based the second detection target image and calculates a second estimated probability representing probability of a detection result;
  detect the region of interest based the third detection target image and calculate a third estimated probability representing probability of a detection result; and
  perform an update using control information used for outputting one of the second estimated probability and the third estimated probability that is higher as the first control information.

2. An endoscope system comprising:
the processing system according to claim 1,
wherein the first control information includes at least one of light source control information for controlling a light source which irradiates an object with illumination light, imaging control information for controlling an imaging condition for capturing the detection target image, and image processing control information for controlling image processing to a signal of the captured image.

3. The endoscope system according to claim 2,
wherein the light source control information includes at least one of a wavelength, light quantity ratio, light quantity, duty, and light distribution of a light source.

4. The endoscope system according to claim 2,
wherein the imaging control information is an imaging frame rate.

5. The endoscope system according to claim 2,
wherein the image processing control information includes at least one information of a color matrix, structure highlighting, noise reduction and automatic gain control.

6. The processing system according to claim 1,
wherein the processor is configured to output the detection result of the region of interest and the estimated probability by inputting the first detection target image to a first trained model.

7. The processing system according to claim 6,
wherein the processor is configured to output a parameter type that should be preferentially changed for improving the estimated probability by inputting the first detection target image and the first control information to a second trained model.

8. The processing system according to claim 7,
wherein the processor is configured to identify the second control information and the third control information based on the parameter type.

9. An endoscope system comprising:
the processing system according to claim 1,
wherein the processor is configured to generate a display image based on image processing control information.

10. The endoscope system according to claim 9,
wherein the processor is configured to acquire the first detection target image and the display image alternately.

11. The endoscope system according to claim 10,
wherein the processor is configured to superpose the detection result of the region of interest and information of the estimated probability on the display image.

12. The processing system according to claim 1,
wherein the processor is configured to:
  extract the region of interest from each frame of the first detection target image; and
  continuously output the detection result of the region of interest.

13. A method performed by a processor, the method comprising:
acquiring a first detection target image generated based on a first control information;
calculating a detection result of a region of interest and estimated probability of the detected result based on the first detection target image;
determining whether or not the estimated probability is equal to or higher than a first threshold;
outputting the detection result of the region of interest in a case where the estimated probability is equal to or higher than the first threshold; and
performing update of the first control information in a case where the estimated probability is less than the first threshold,
wherein performing the update of the first control information comprises:
  identifying a second control information and a third control information based on the first detection target image and the first control information;
  acquiring a second detection target image based on the second control information;
  acquiring a third detection target image based on the third control information;

detecting the region of interest based the second detection target image and calculates a second estimated probability representing probability of a detection result;

detecting the region of interest based the third detection target image and calculate a third estimated probability representing probability of a detection result; and performing an update using control information used for outputting one of the second estimated probability and the third estimated probability that is higher as the first control information.

14. A non-transitory computer-readable storage medium storing instructions that cause a computer to at least perform:

acquiring a first detection target image generated based on a first control information;

calculating a detection result of a region of interest and estimated probability of the detected result based on the first detection target image;

determining whether or not the estimated probability is equal to or higher than a first threshold;

outputting the detection result of the region of interest in a case where the estimated probability is equal to or higher than the first threshold; and performing update of the first control information in a case where the estimated probability is less than the first threshold, wherein performing the update of the first control information comprises:

identifying a second control information and a third control information based on the first detection target image and the first control information;

acquiring a second detection target image based on the second control information;

acquiring a third detection target image based on the third control information;

detecting the region of interest based the second detection target image and calculates a second estimated probability representing probability of a detection result;

detecting the region of interest based the third detection target image and calculate a third estimated probability representing probability of a detection result; and performing an update using control information used for outputting one of the second estimated probability and the third estimated probability that is higher as the first control information.

\* \* \* \* \*